US010179839B2

(12) United States Patent
Falkowski et al.

(10) Patent No.: US 10,179,839 B2
(45) Date of Patent: Jan. 15, 2019

(54) SULFUR TERMINATED ORGANOSILICA MATERIALS AND USES THEREOF

(71) Applicant: ExxonMobil Research and Engineering Company, Annandale, NJ (US)

(72) Inventors: Joseph M. Falkowski, Hampton, NJ (US); Mobae Afeworki, Phillipsburg, NJ (US); David C. Calabro, Bridgewater, NJ (US); David A. Griffin, Phillipsburg, NJ (US); Simon C. Weston, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/802,680

(22) Filed: Nov. 3, 2017

(65) Prior Publication Data
US 2018/0142066 A1 May 24, 2018

Related U.S. Application Data

(60) Provisional application No. 62/424,027, filed on Nov. 18, 2016.

(51) Int. Cl.
*C08G 77/02* (2006.01)
*C07C 5/10* (2006.01)
(Continued)

(52) U.S. Cl.
CPC ............ *C08G 77/02* (2013.01); *B01J 20/223* (2013.01); *B01J 20/262* (2013.01); *B01J 23/50* (2013.01);
(Continued)

(58) Field of Classification Search
None
See application file for complete search history.

(56) References Cited

U.S. PATENT DOCUMENTS 2,653,959 A 9/1953 Moore et al.
2,943,105 A 6/1960 Caruthers
(Continued)

FOREIGN PATENT DOCUMENTS

CN 101804335 A 8/2010
CN 101980013 A 2/2011
(Continued)

OTHER PUBLICATIONS

Hatton et al. Past, Present, and Future of Periodic Mesoporous Organosilica—The PMOs, Acc. Chem. Res. 2005, 38, 305-312. (Year: 2005).*

(Continued)

*Primary Examiner* — Robert S Loewe
(74) *Attorney, Agent, or Firm* — Andrew T. Ward

(57) ABSTRACT

Provided herein are compositions and methods for use of an organosilica material comprising a copolymer of at least one monomer of Formula $[R^1R^2SiCH_2]_3$ (I), wherein, $R^1$ represents a $C_1$-$C_4$ alkoxy group; and $R^2$ is a $C_1$-$C_4$ alkoxy group or a $C_1$-$C_4$ alkyl group; and at least one other monomer of Formula $[(Z^1O)_xZ^2_{3-x}Si—Z^3—SZ^4]$ (II), wherein, $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon; $Z^4$ is either H or $O_3H$; and x represents any one of integers 1, 2, and 3. The composition may be used as a support material to covalently attach transition metal cations, as a sorbent for olefin/paraffin separations, as a catalyst support for hydrogenation reactions, as a precursor for highly dispersed metal nanoparticles, or as a polar sorbent for crude feeds.

15 Claims, 7 Drawing Sheets

(51) Int. Cl.
  *B01J 20/26* (2006.01)
  *C07C 7/12* (2006.01)
  *B01J 20/22* (2006.01)
  *B01J 23/50* (2006.01)
  *B01J 31/06* (2006.01)
  *C08J 9/28* (2006.01)

(52) U.S. Cl.
  CPC ............... *B01J 31/069* (2013.01); *C07C 5/10* (2013.01); *C07C 7/12* (2013.01); *C08J 9/286* (2013.01); *C07C 2523/50* (2013.01); *C07C 2531/06* (2013.01); *C08J 2201/0504* (2013.01); *C08J 2205/022* (2013.01); *C08J 2205/042* (2013.01); *C08J 2205/10* (2013.01); *C08J 2383/02* (2013.01)

(56) References Cited

U.S. PATENT DOCUMENTS

| | | | |
|---|---|---|---|
| 3,178,392 | A | 4/1965 | Kriner |
| 3,489,808 | A | 1/1970 | Eberly, Jr. |
| 3,931,350 | A | 1/1976 | Sparks |
| 4,218,308 | A | 8/1980 | Itoh et al. |
| 4,337,156 | A | 6/1982 | DeRosset |
| 5,245,107 | A | 9/1993 | Yon et al. |
| 5,365,003 | A | 11/1994 | Chang et al. |
| 5,630,937 | A | 5/1997 | Betz et al. |
| 5,719,322 | A | 2/1998 | Lansbarkis et al. |
| 6,051,631 | A | 4/2000 | Hottovy |
| 6,111,162 | A | 8/2000 | Rossini et al. |
| 6,118,037 | A | 9/2000 | Piccoli et al. |
| 6,632,766 | B2 | 10/2003 | Kanazirev |
| 6,790,344 | B1 | 9/2004 | Min et al. |
| 6,987,152 | B1 | 1/2006 | Eisinger et al. |
| 7,102,044 | B1 | 9/2006 | Kulprathipanja et al. |
| 7,141,630 | B2 | 11/2006 | Vizzini et al. |
| 7,300,905 | B2 | 11/2007 | Keefer et al. |
| 7,326,821 | B2 | 2/2008 | Risch et al. |
| 7,368,618 | B2 | 5/2008 | Kulprathipanja et al. |
| 7,497,965 | B2 | 3/2009 | Wariishi et al. |
| 7,538,065 | B2 | 5/2009 | McCarthy et al. |
| 7,576,248 | B2 | 8/2009 | Kulprathipanja et al. |
| 7,682,502 | B2 | 3/2010 | McCarthy et al. |
| 7,705,062 | B2 | 4/2010 | Markowitz et al. |
| 7,754,330 | B2 | 7/2010 | Hamada et al. |
| 7,767,620 | B2 | 8/2010 | Whitnall et al. |
| 7,947,799 | B2 | 5/2011 | Manfred et al. |
| 7,959,720 | B2 | 6/2011 | Deckman et al. |
| 8,110,692 | B2 | 2/2012 | Bellussi et al. |
| 8,211,498 | B2 | 7/2012 | Ku et al. |
| 8,277,600 | B2 | 10/2012 | Hamada et al. |
| 8,277,661 | B2 | 10/2012 | Sah et al. |
| 8,425,762 | B2 | 4/2013 | McCarthy et al. |
| 8,441,006 | B2 | 5/2013 | Michalak et al. |
| 8,444,750 | B2 | 5/2013 | Deckman et al. |
| 8,470,074 | B2 | 6/2013 | Baugh et al. |
| 8,529,662 | B2 | 9/2013 | Kelley et al. |
| 8,529,663 | B2 | 9/2013 | Reyes et al. |
| 8,545,602 | B2 | 10/2013 | Chance et al. |
| 8,545,694 | B2 | 10/2013 | McCarthy et al. |
| 8,562,856 | B2 | 10/2013 | Giannantonio et al. |
| 8,568,520 | B2 | 10/2013 | Ohashi et al. |
| 8,598,070 | B1 | 12/2013 | Baugh et al. |
| 8,598,071 | B1 | 12/2013 | Baugh et al. |
| 8,784,533 | B2 | 7/2014 | Leta et al. |
| 8,784,534 | B2 | 7/2014 | Kamakoti et al. |
| 8,784,535 | B2 | 7/2014 | Ravikovitch et al. |
| 8,809,561 | B2 | 8/2014 | Bellussi et al. |
| 8,858,683 | B2 | 10/2014 | Deckman |
| 9,005,561 | B2 | 4/2015 | Leta et al. |
| 9,034,079 | B2 | 5/2015 | Deckman et al. |
| 9,181,282 | B2 | 11/2015 | Ide et al. |
| 9,382,344 | B2 | 7/2016 | Ho et al. |
| 2002/0147377 | A1 | 10/2002 | Kanazirev |
| 2003/0188991 | A1 | 10/2003 | Shan et al. |
| 2005/0093189 | A1 | 5/2005 | Vo |
| 2006/0058565 | A1 | 3/2006 | De Wild |
| 2006/0070917 | A1 | 4/2006 | McCarthy et al. |
| 2007/0034992 | A1 | 2/2007 | Wariishi et al. |
| 2007/0054136 | A1 | 3/2007 | Takahashi et al. |
| 2007/0112242 | A1 | 5/2007 | Edmiston |
| 2007/0173401 | A1 | 7/2007 | Landskron et al. |
| 2009/0130412 | A1 | 5/2009 | Hatton et al. |
| 2009/0215612 | A1 | 8/2009 | McCarthy et al. |
| 2009/0294922 | A1 | 12/2009 | Hamada et al. |
| 2010/0155302 | A1 | 6/2010 | Kaminsky et al. |
| 2010/0233482 | A1 | 9/2010 | Hamada et al. |
| 2011/0139685 | A1 | 6/2011 | McCarthy et al. |
| 2011/0190115 | A1 | 8/2011 | Ciriminna et al. |
| 2012/0059181 | A1 | 3/2012 | Bellussi et al. |
| 2012/0160742 | A1 | 6/2012 | Sohn et al. |
| 2013/0032716 | A1 | 2/2013 | Nakasuji et al. |
| 2013/0075876 | A1 | 3/2013 | Goethals et al. |
| 2013/0078172 | A1 | 3/2013 | Bingbing et al. |
| 2013/0249049 | A1 | 9/2013 | Michalak et al. |
| 2014/0004358 | A1 | 1/2014 | Blackwell et al. |
| 2014/0186246 | A1 | 7/2014 | Calabro et al. |
| 2014/0208753 | A1 | 7/2014 | Liu et al. |
| 2015/0005525 | A1* | 1/2015 | Ide .................. B01J 20/283 556/406 |
| 2015/0011787 | A1 | 1/2015 | Bellussi et al. |
| 2016/0167015 | A1 | 6/2016 | Podsiadlo et al. |
| 2016/0167016 | A1 | 6/2016 | Li et al. |
| 2016/0167032 | A1 | 6/2016 | Podsiadlo et al. |
| 2016/0168171 | A1 | 6/2016 | Li et al. |
| 2016/0168172 | A1 | 6/2016 | Li et al. |
| 2016/0168173 | A1 | 6/2016 | Li et al. |
| 2016/0168174 | A1 | 6/2016 | Li et al. |
| 2016/0168333 | A1 | 6/2016 | Podsiadlo et al. |
| 2016/0168484 | A1 | 6/2016 | Weigel et al. |
| 2016/0168485 | A1 | 6/2016 | Li et al. |
| 2016/0229959 | A1 | 8/2016 | Li et al. |
| 2017/0173561 | A1* | 6/2017 | Lawrence ............... B01J 20/289 |
| 2017/0306068 | A1 | 10/2017 | Holtcamp et al. |
| 2017/0313791 | A1 | 11/2017 | Mertens et al. |
| 2017/0320971 | A1 | 11/2017 | Holtcamp et al. |
| 2017/0320977 | A1 | 11/2017 | Holtcamp et al. |
| 2017/0327604 | A1 | 11/2017 | Holtcamp et al. |
| 2017/0354961 | A1 | 12/2017 | Podsiadlo et al. |
| 2017/0355822 | A1 | 12/2017 | Calabro et al. |
| 2017/0355823 | A1 | 12/2017 | Peterson et al. |
| 2018/0142066 | A1 | 5/2018 | Falkowski et al. |

FOREIGN PATENT DOCUMENTS

| | | |
|---|---|---|
| CN | 102052713 A | 5/2011 |
| CN | 102643429 A | 8/2012 |
| CN | 103495340 A | 1/2014 |
| CN | 103613975 A | 3/2014 |
| CN | 104117343 A | 10/2014 |
| CN | 103157362 A | 6/2016 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9610537 A1 | 4/1996 |
| WO | 2004033507 A1 | 4/2004 |
| WO | 2006032140 A1 | 3/2006 |
| WO | 2007081212 A1 | 7/2007 |
| WO | 2011145933 A1 | 11/2011 |
| WO | 2013093022 A1 | 6/2013 |
| WO | 2014040512 A1 | 1/2014 |

(56) References Cited

FOREIGN PATENT DOCUMENTS

| WO | 2014090757 | A1 | | 6/2014 | | |
|----|------------|-----|---|--------|---|---|
| WO | 2015100198 | A1 | | 7/2015 | | |
| WO | 2016094784 | A1 | | 6/2016 | | |
| WO | 2016094803 | A1 | | 6/2016 | | |
| WO | WO-2016094848 | A1 | * | 6/2016 | ............... | C08F 2/10 |
| WO | WO-2016094861 | A1 | * | 6/2016 | ............... | C08F 2/10 |
| WO | WO-2016094866 | A1 | * | 6/2016 | ............... | C08F 2/10 |
| WO | WO-2016094870 | A1 | * | 6/2016 | ............... | C08F 2/10 |
| WO | WO-2016094843 | A3 | * | 11/2016 | ............... | C08F 4/02 |

OTHER PUBLICATIONS

Landskron et al., "Periodic Mesoporous Organosilicas Containing Interconnected [Si(CH2)]3 Rings", Science, Oct. 10, 2003, pp. 266-269, vol. 302, Ameri8can Association for the Advancement of Science.

Margolese et al., "Direct Syntheses of Ordered SBA-15 Mesoporous Silica Containing Sulfonic Acid Groups", Chemistry of Materials, 2000, pp. 2448-2459, vol. 12, iss. 8, ACS Publications.

Shen et al., "Sulfonic Acid-functionalized Mesoporous Silica: Synthesis, Characterization, and Catalytic Reaction of Alcohol Coupling to Ethers", Journal of Physical Chemistry B, Oct. 3, 2002, pp. 9975-9978, vol. 106, iss. 39, ACS Publications.

Kang et al., "Highly Selective Adsorption of Pt2+ and Pd2+ using Thiol-Functionalized Mesoporous Silica", Industrial & Engineering Chemistry Research, Mar. 17, 2004, pp. 1478-1484, vol. 43, iss. 6, ACS Publications.

Das et al., "Sulfonic acid functionalized mesoporous MCM-41 silica as a convenient catalyst for Bisophenol-A synthesis", Chemical Communication, Oct. 5, 2001, pp. 2178-2179, Royal Society of Chemistry.

Topchiev et al., "Preparation of hexa alkoxy derivatives of cyclotrimethylenesilane", Doklady Akademii Nauk SSSR, 1955, pp. 95-96. vol. 103.

Kriner, "The preparation of cyclic siliconmethylene compounds", Journal of Organic Chemistry, Jun. 1964, pp. 1601-1606, vol. 29.

Kuivila et al., "Trimethylsilyl-substituted norbornenes, norbornanes, and nortricyclene", Journal of Organic Chemistry, Oct. 1964, pp. 2845-2851, vol. 29.

Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.

Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.

Melde et al., "Mesoporous Sieves with Unified Hybrid Inorganic/Organic Frameworks", Chemistry of Materials, Oct. 9, 1999, pp. 3302-3308, vol. 11.

Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.

Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.

"Vidal et al., ""Adsorption of polycyclic aromatic hydrocarbons from aqueous solutions by modified periodic mesoporous organosilica""", Journal of Colloid and Interface Science, Feb. 3, 2011, pp. 466-473, vol. 357, No. 2."

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.

Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.

Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.

"Poli et al., ""Different Routes for Preparing Mesoporous Organosilicas Containing the Troger 's Base and Their Textural and Catalytic Implications""", The Journal of Physical Chemistry C, Apr. 21, 2011, pp. 7573-7585, vol. 115, No. 15, ACS Publications."

PCT/US2015/065208 International Search Report and Written Opinion dated May 17, 2016.

PCT/US2015/065200 Partial International Search Report and Written Opinion dated May 23, 2016.

"Diaz et al., ""Hybrid organic-inorganic catalytic porous materials synthesized at neutral pH in absence of structural directing agents""", Journal of Materials Chemistry, Jan. 1, 2009, pp. 5970-5979, vol. 19, No. 33, Royal Society of Chemistry."

Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.

PCT/US2015/065200 Partial International Search Report and Written Opinion dated Jul. 18, 2016.

Goethals et al., "Ultra-low-k cyclic carbon-bridged PMO films with a high chemical resistance", Journal of Materials Chemistry, Feb. 21, 2012, pp. 8281-8286, vol. 22.

PCT/US2015/065258 Partial International Search Report and Written Opinion dated Mar. 16, 2016.

PCT/US2015/065194 International Search Report and Written Opinion dated Mar. 29, 2016.

PCT/US2015/065191 International Search Report and Written Opinion dated Mar. 29, 2016.

PCT/US2015/065306 International Search Report and Written Opinion dated Mar. 29, 2016.

PCT/US2015/065219 International Search Report and Written Opinion dated Apr. 5, 2016.

PCT/US2015/065283 International Search Report and Written Opinion dated Apr. 6, 2016.

PCT/US2015/065199 International Search Report and Written Opinion dated Apr. 8, 2016.

PCT/US2015/065204 International Search Report and Written Opinion dated Apr. 8, 2016.

PCT/US2015/065225 International Search Report and Written Opinion dated Apr. 8, 2016.

Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.

Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.

Eliseeva et al., "Antifoaming additive for alkaline absorption solutions for removal of carbon dioxide from synthesis gas", Khimicheskaya Promyshlennost, 1999, pp. 632-633, vol. 10.

Brondani et al., "Polyfunctional carbosilanes and organosilicon compounds. Synthesis via Grignard reactions", Tetrahedron Letters, Mar. 2, 2001, pp. 2111-2114, vol. 34.

Gilman et al., "Reactions of triphenylsilyllithium with some dichloropropenes", Journal of Organometallic Chemistry, Apr. 13, 2001, pp. 293-303, vol. 2.

Goethals, et al., "A new procedure to seal the pores of mesoporous low-k films with precondensed organosilica oligomers", Chemical Communications, 2012, pp. 2797-2799, vol. 48, No. 22, Royal Society of Chemistry.

Goethals et al., "Sealed ultra low-k organosilica films with improved electrical, mechanical and chemical properties", Journal of Materials Chemistry C, 2013, vol. 1, No. 25, Royal Society of Chemistry.

Goethals et al., "Hydrophobic high quality ring PMOs with an extremely high stability", Journal of Materials Chemistry, 2010, pp. 1709-1716, vol. 20, No. 9, Royal Society of Chemistry.

Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.

(56) References Cited

OTHER PUBLICATIONS

Bahuleyan et al., "One-pot synthesis of spherical periodic mesoporous organosilica supported catalyst bearing Ni(II) α-diimine comple1es for ethylene polymerization", Catalysis Communications, 2009, pp. 252-256, vol. 11.

\* cited by examiner

SULFUR TERMINATED ORGANOSILICA MATERIALS AND USES THEREOF

CROSS-REFERENCE TO RELATED APPLICATIONS

This application claims the benefit of U.S. Provisional Application No. 62/424,027, filed on Nov. 18, 2016, the entire contents of which are incorporated herein by reference.

This application is also related to the following other U.S. Patent Application Publications all filed on Dec. 11, 2015: US2016/0168173 A1; US2016/0168171 A1; US2016/0167032 A1; US2016/0168172 A1; US2016/0168174 A1; US2016/0229959 A1; US2016/0168333 A1; US2016/0167016 A1; US2016/0168485 A1; US2016/0167015 A1; and US2016/0168484 A1, the entire disclosures of each of which are incorporated by reference herein.

Additionally, this application is further related to following other co-pending PCT Patent Application Publications, all filed on Dec. 11, 2015: WO2016/094870 A1; WO2016/094861 A1; WO2016/094866 A1; WO2016/094843 A1; and WO2016/094848 A1, the entire disclosures of each of which are incorporated by reference herein.

FIELD

The present disclosure relates to organosilica materials, methods of making and uses thereof.

BACKGROUND

Porous inorganic solids have found great utility as catalysts and separation media for industrial application. In particular, mesoporous materials, such as silicas and aluminas, having a periodic arrangement of mesopores are attractive materials for use in adsorption, separation and catalysis processes due to their uniform and tunable pores, high surface areas and large pore volumes. The pore structure of such mesoporous materials is large enough to absorb large molecules and the pore wall structure can be as thin as about 1 nm. Further, such mesoporous materials are known to have large specific surface areas (e.g., 1000 m$^2$/g) and large pore volumes (e.g., 1 cm$^3$/g). For these reasons, such mesoporous materials enable reactive catalysts, adsorbents composed of a functional organic compound, and other molecules to rapidly diffuse into the pores and therefore, can be advantageous over zeolites, which have smaller pore sizes. Consequently, such mesoporous materials can be useful not only for catalysis of high-speed catalytic reactions, but also as large capacity adsorbents.

It was further discovered that the inclusion of some organic groups in the mesoporous framework can provide adjustable reactive surfaces and also contributes to uniformity in pore size, higher mechanical strength, and hydrothermal stability of the material. Thus, mesoporous organosilica materials can exhibit unique properties compared to mesoporous silica such as enhanced hydrothermal stability, chemical stability, and mechanical properties. Organic groups can be incorporated using bridged silsesquioxane precursors of the form Si—R—Si to form mesoporous organosilicas.

Mesoporous organosilicas are conventionally formed by the self-assembly of the silsequioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science,* 302:266-269 (2003)] report the self-assembly of 1,3,5-tris[diethoxysila]cylcohexane [(EtO)$_2$ SiCH$_2$]$_3$ in the presence of a base and the structure directing agent, cetyltrimethylammonium bromide to form PMOs that are bridged organosilicas with a periodic mesoporous framework, which consist of SiO$_3$R or SiO$_2$R$_2$ building blocks, where R is a bridging organic group. In PMOs, the organic groups can be homogeneously distributed in the pore walls. U.S. Patent Application Publication No. 2012/0059181 reports the preparation of a crystalline hybrid organic-inorganic silicate formed from 1,1,3,3,5,5-hexaethoxy-1,3,5-trisilacyclohexane in the presence of NaAlO$_2$ and base. U.S. Patent Application Publication No. 2007/003492 reports preparation of a composition formed from 1,1,3,3,5,5-hexaethoxy-1,3,5-trisilacyclohexane in the presence of propylene glycol monomethyl ether.

However, the use of a structure directing agent, such as a surfactant, in the preparation of an organosilica material, such as a PMO, requires a complicated, energy intensive process to eliminate the structure directing agent at the end of the preparation process. This limits the ability to scale-up the process for industrial applications. Therefore, there is a need to provide additional organosilica materials with a desirable pore diameter, pore volume and surface area. Further, there is a need to provide such organosilica materials that can be prepared by a method that can be practiced in the absence of a structure directing agent, a porogen or surfactant.

U.S. Patent Application Publication No. US2016/0168174 describes a method to provide such organosilica materials by a method practiced in the absence of a structure directing agent, porogen, or surfactant. The materials and methods described therein, however, do not provide guidance regarding incorporation of organic functional moieties (thiols, sulfonic acids, etc.) to improve the utility of the materials as solid acid or metal supports. Thus, there is a need to provide such organosilica materials with increased functionality without the need for a structure directing agent, a porogen or surfactant.

SUMMARY

It has been found that an organosilica material with desirable pore diameter, pore volume, and surface area can be achieved. Further, such organosilica material can be successfully prepared without the need for a structure directing agent, a porogen or surfactant.

In one aspect, described herein is an organosilica material comprising a copolymer of at least one monomer of Formula [R$^1$R$^2$SiCH$_2$]$_3$ (I), wherein, R$^1$ represents a C$_1$-C$_4$ alkoxy group; and R$^2$ is a C$_1$-C$_4$ alkoxy group or a C$_1$-C$_4$ alkyl group; and at least one other monomer of Formula [(Z$^1$O)$_x$ Z$^2$$_{3-x}$Si—Z$^3$—SZ$^4$] (II), wherein, Z$^1$ represents a hydrolysable functional group; Z$^2$ represents a C$_1$-C$_{10}$ alkyl or aryl group; Z$^3$ represents a C$_2$-C$_{11}$ cyclic or linear hydrocarbon; Z$^4$ is either H or O$_3$H; and x represents any one of integers 1, 2, and 3.

In another aspect, the Z$^3$ has incorporated within the C$_2$-C$_{11}$ cyclic or linear hydrocarbon (i) an amine, (ii) an ether, (iii) a heteroatom, or (iv) a combination of any of (i), (ii), and (iii), provided that Si and S remain bonded to a carbon atom.

The organosilica material provided herein may further comprise a catalyst metal, e.g. a transition metal, metal oxide, and/or metal sulfide. In some embodiments, silver or copper are preferred catalyst metals. The catalyst metal may be incorporated into the organosilica material as dispersed metal particles.

Also provided are methods for use of the organosilica materials provided in various refinery separations schemes. For example, in one aspect, the thiol or sulfonic acid terminated organosilica materials of the present disclosure can be used for separation of olefins from paraffins in hydrocarbon streams comprising olefins and paraffins. In another aspect, the materials described herein can be used as a hydrogenation catalyst in the presence of a hydrogen containing treat gas in a reaction stage operated under effective hydrogenation conditions. In yet another aspect, the materials described herein can be used as a sorbent for separation of polar organic compounds from a hydrocarbon feed. The composition may be further utilized used as a support material to covalently attach transition metal cations and as a precursor for highly dispersed metal nanoparticles.

Other embodiments, including particular aspects of the embodiments summarized above, will be evident from the detailed description that follows.

DETAILED DESCRIPTION

Figure 1:
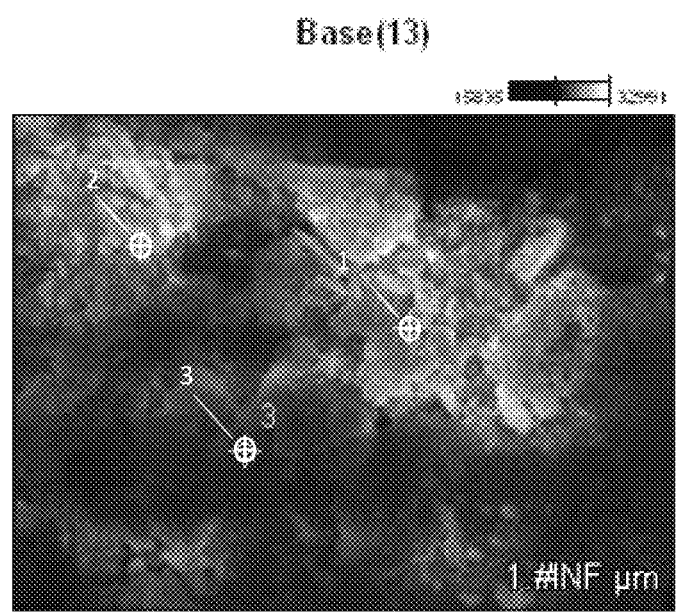
FIG. 1 is a scanning electron micrograph (SEM) of an exemplary composition disclosed herein.

In various aspects of the present disclosure, organosilica materials, methods for preparing organosilica materials and gas and liquid separation processes using the organosilica materials are provided.

I. Definitions

For purposes of the present disclosure including the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "hydrolysable" means capable of undergoing hydrolysis. In the context generally used here, hydrolysable moieties A-X, are capable of reacting with water to replace X with a hydroxyl group according to the reaction:

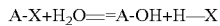

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$—$CH(CH_3)_2$) and "$C_4$ alkyl" refers to butyl (e.g. —$CH_2CH_2CH_2CH_3$, $CHCH_2CH_3$, —$CH_2$—($CH_3$)CH ($CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

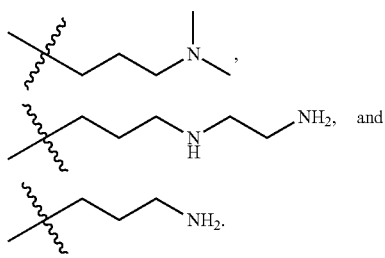

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

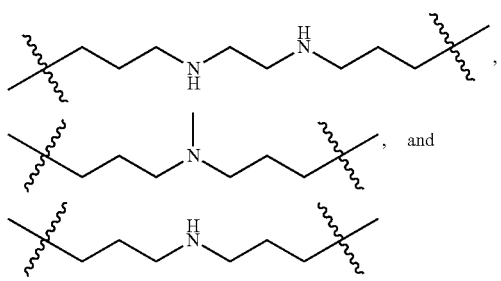

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH═CH—, —CH═CHCH$_2$—, —CH═CH—CH—, —CH$_2$CH$_2$CH═CHCH$_2$—, etc. —CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompassses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenylmethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the term "thiol" refers to a SH group.

As used herein, the terms "structure directing agent," "SDA," "surfactant," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Organosilica Materials

The present disclosure relates to organosilica materials with a terminal thiol group. The organosilica material may be a copolymer of at least one independent monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group; and at least one other monomer selected of Formula $[(Z^1O)_xZ^2_{3-x}Si—Z^3—SZ^4]$(II), wherein $Z^1$ represents a hydrolysable functional group, $Z^2$ represents a $C_1$-$C_{10}$ alkyl or aryl group, $Z^3$ represents a $C_2$-$C_{11}$ cyclic or linear hydrocarbon, $Z^4$ is either H or $O_3H$, and x represents any one of integers 1, 2, and 3. It will be appreciated by those of skill in the art that $Z^3$ may have incorporated within the $C_2$-$C_{11}$ cyclic or linear hydrocarbon (i) an amine, (ii) an ether, (iii) a heteroatom, or (iv) a combination of any of (i), (ii), and (iii), provided that Si and S remain bonded to a carbon atom.

II.A. Monomers of Formula (I)

In various embodiments, $R^1$ can be a $C_1$-$C_4$ alkoxy group and $R^2$ can be a $C_1$-$C_4$ alkoxy group or a $C_1$-$C_4$ alkyl group.

In one embodiment, $R^1$ can comprise a $C_1$-$C_3$ alkoxy or methoxy or ethoxy.

Additionally or alternatively, $R^2$ can comprise a $C_1$-$C_4$ alkoxy, a $C_1$-$C_3$ alkoxy or methoxy or ethoxy. Additionally or alternatively, $R^2$ can comprise methyl, ethyl or propyl, such as a methyl or ethyl.

Additionally or alternatively, $R^1$ can be a $C_1$-$C_2$ alkoxy group and $R^2$ can be a $C_1$-$C_2$ alkoxy group or a $C_1$-$C_2$ alkyl group.

Additionally or alternatively, $R^1$ can be methoxy or ethoxy and $R^2$ can be methyl or ethyl.

In a particular embodiment, $R^1$ and $R^2$ can be ethoxy, such that the compound corresponding to Formula (I) can be 1,1,3,3,5,5-hexaethoxy-1,3,5-trisilacyclohexane, $([(EtO)_2SiCH_2]_3)$.

In a particular embodiment, $R^1$ can be ethoxy and $R^2$ can be methyl, such that compound corresponding to Formula (I) can be 1,1,3,3,5,5-hexaethoxy-1,3,5-trisilacyclohexane, $([EtOCH_3SiCH_2]_3)$.

II.B. Monomers of Formula (II)

In various embodiments, the organosilica material may further comprise another monomer in combination with independent monomer of Formula (I), such as another monomer having at least one independent monomer of Formula $[(Z^1O)_xZ^2_{3-x}Si—Z^3—SZ^4]$ (II), wherein each $Z^1O$ is a hydrolysable functional group, meaning a functional group that is capable of undergoing hydrolysis. $Z^2$ represents a $C_1$-$C_{10}$ alkyl or aryl group; $Z^3$ represents a $C_2$-$C_{11}$ cyclic or linear hydrocarbon; $Z^4$ is either H or $O_3H$, and x represents any one of integers 1, 2, and 3.

In various aspects, $Z^2$ can be a $C_1$-$C_{10}$ alkyl group, a $C_1$-$C_9$ alkyl group, a $C_1$-$C_8$ alkyl group, a $C_1$-$C_7$ alkyl group, a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl.

Additionally or alternatively, $Z^2$ can be a $C_6$-$C_{10}$ aryl group.

Additionally or alternatively, $Z^3$ can be a $C_2$-$C_{12}$ cyclic or linear hydrocarbon.

Additionally or alternatively, $Z^3$ can be a $C_2$-$C_{12}$ alkyl group, a $C_2$-$C_{12}$ alkylene group, a $C_2$-$C_{12}$ nitrogen containing alkyl, a $C_2$-$C_{12}$ nitrogen containing alkylene group, a $C_2$-$C_{12}$ alkenyl group, a $C_2$-$C_{12}$ alkenylene group, a $C_2$-$C_{12}$ alkynyl group, or a $C_2$-$C_{12}$ alkynylene group.

Additionally or alternatively, $Z^3$ can be a $C_6$-$C_{12}$ aryl group, a $C_2$-$C_{12}$ aralkyl group, a $C_4$-$C_{12}$ heterocyclo group, or a $C_4$-$C_{12}$ heterocycloalkyl group.

Additionally or alternatively, $Z^3$ can be a $C_2$-$C_{11}$ cyclic or linear hydrocarbon which has an amine, an ether, a heteroatom, or any combination of amine, ether, or heteroatom incorporated within it.

In a particular embodiment, Formula (II) can be 3-(triethoxysilyl)propane-1-thiol.

The organosilica materials made by the methods described herein can be characterized as described in the following sections.

II.C. X-Ray Diffraction Peaks

The organosilica materials described herein can exhibit powder X-ray diffraction patterns (using Cu Kα radiation) with one broad peak between about 1 and about 4 degrees 2θ, particularly one peak between about 1 and about 3 degrees 2θ. In the 0.5 to 12 degrees 2θ range, the organosilica materials can exhibit substantially no peaks. The organosilica materials can exhibit substantially no peaks in the range of about 3 to about 12 degrees 2θ, about 4 to about 12 degrees 2θ, in the range of about 5 to about 12 degrees 2θ, in the range of about 6 to about 12 degrees 2θ, in the range of about 7 to about 12 degrees 2θ, in the range of about 8 to about 12 degrees 2θ, in the range of about 9 to about 12 degrees 2θ, in the range of about 10 to about 12 degrees 2θ, or in the range of about 11 to about 12 degrees 2θ.

II.D. Silanol Content

The organosilica materials obtainable by the methods described herein can have a silanol content that varies within wide limits, depending on the composition of the synthesis solution. The silanol content can conveniently be determined by solid state silicon NMR.

In various aspects, the organosilica material can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica material may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

II.E. Pore Size

The organosilica material described herein are advantageously in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material can alternatively have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Alternatively, the organosilica material can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica material can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica material can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organosilica material described herein can have an average pore diameter of about 1.0 nm to about 30.0 nm, particularly about 1.0 nm to about 25.0 nm, particularly about 2.0 nm to about 25.0 nm, particularly about 2.0 nm to about 20.0 nm, particularly about 2.0 nm to about 15.0 nm, particularly about 2.0 nm to about 10.0 nm, or particularly about 3.0 nm to about 10.0 nm.

II.F. Surface Area

The surface area of the organosilica material can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface area as determined by the BET method.

In various embodiments, the organosilica material can have a total surface area greater than or equal to about 100 m$^2$/g, greater than or equal to about 200 m$^2$/g, greater than or equal to about 300 m$^2$/g, greater than or equal to about 400 m$^2$/g, greater than or equal to about 450 m$^2$/g, greater than or equal to about 500 m$^2$/g, greater than or equal to about 550 m$^2$/g, greater than or equal to about 600 m$^2$/g, greater than or equal to about 700 m$^2$/g, greater than or equal to about 800 m$^2$/g, greater than or equal to about 850 m$^2$/g, greater than or equal to about 900 m$^2$/g, greater than or equal to about 1,000 m$^2$/g, greater than or equal to about 1,050 m$^2$/g, greater than or equal to about 1,100 m$^2$/g, greater than or equal to about 1,150 m$^2$/g, greater than or equal to about 1,200 m$^2$/g, greater than or equal to about 1,250 m$^2$/g, greater than or equal to about 1,300 m$^2$/g, greater than or equal to about 1,400 m$^2$/g, greater than or equal to about 1,450 m$^2$/g, greater than or equal to about 1,500 m$^2$/g, greater than or equal to about 1,550 m$^2$/g, greater than or equal to about 1,600 m$^2$/g, greater than or equal to about 1,700 m$^2$/g, greater than or equal to about 1,800 m$^2$/g, greater than or equal to about 1,900 m$^2$/g, greater than or equal to about 2,000 m$^2$/g, greater than or equal to greater than or equal to about 2,100 m$^2$/g, greater than or equal to about 2,200 m$^2$/g, greater than or equal to about 2,300 m$^2$/g or about 2,500 m$^2$/g.

Additionally or alternatively, the organosilica material may have a total surface area of about 50 m$^2$/g to about 2,500 m$^2$/g, about 50 m$^2$/g to about 2,000 m$^2$/g, about 50 m$^2$/g to about 1,500 m$^2$/g, about 50 m$^2$/g to about 1,000 m$^2$/g, about 100 m$^2$/g to about 2,500 m$^2$/g, about 100 m$^2$/g to about 2,300 m$^2$/g, about 100 m$^2$/g to about 2,200 m$^2$/g, about 100 m$^2$/g to about 2,100 m$^2$/g, about 100 m$^2$/g to about 2,000 m$^2$/g, about 100 m$^2$/g to about 1,900 m$^2$/g, about 100 m$^2$/g to about 1,800 m$^2$/g, about 100 m$^2$/g to about 1,700 m$^2$/g, about 100 m$^2$/g to about 1,600 m$^2$/g, about 100 m$^2$/g to about 1,550 m$^2$/g, about 100 m$^2$/g to about 1,500 m$^2$/g, about 100 m$^2$/g to about 1,450 m$^2$/g, about 100 m$^2$/g to about 1,400 m$^2$/g, about 100 m$^2$/g to about 1,300 m$^2$/g, about 100 m$^2$/g to about 1,250 m$^2$/g, about 100 m$^2$/g to about 1,200 m$^2$/g, about 100 m$^2$/g to about 1,150 m$^2$/g, about 100 m$^2$/g to about 1,100 m$^2$/g, about 100 m$^2$/g to about 1,050 m$^2$/g, about 100 m$^2$/g to about 1,000 m$^2$/g, about 100 m$^2$/g to about 900 m$^2$/g, about 100 m$^2$/g to about 850 m$^2$/g, about 100 m$^2$/g to about 800 m$^2$/g, about 100 m$^2$/g to about 700 m$^2$/g, about 100 m$^2$/g to about 600 m$^2$/g, about 100 m$^2$/g to about 550 m$^2$/g, about 100 m$^2$/g to about 500 m$^2$/g, about 100 m$^2$/g to about 450 m$^2$/g, about 100 m$^2$/g to about 400 m$^2$/g, about 100 m$^2$/g to about 300 m$^2$/g, about 100 m$^2$/g to about 200 m$^2$/g, about 200 m$^2$/g to about 2,500 m$^2$/g, about 200 m$^2$/g to about 2,300 m$^2$/g, about 200 m$^2$/g to about 2,200 m$^2$/g, about 200 m$^2$/g to about 2,100 m$^2$/g, about 200 m$^2$/g to about 2,000 m$^2$/g, about 200 m$^2$/g to about 1,900 m$^2$/g, about 200 m$^2$/g to about 1,800 m$^2$/g, about 200 m$^2$/g to about 1,700 m$^2$/g, about 200 m$^2$/g to about 1,600 m$^2$/g, about 200 m$^2$/g to about 1,550 m$^2$/g, about 200 m$^2$/g to about 1,500 m$^2$/g, about 200 m$^2$/g to about 1,450 m$^2$/g, about 200 m$^2$/g to about 1,400 m$^2$/g, about 200 m$^2$/g to about 1,300 m$^2$/g, about 200 m$^2$/g to about 1,250 m$^2$/g, about 200 m$^2$/g to about 1,200 m$^2$/g, about 200 m$^2$/g to about 1,150 m$^2$/g, about 200 m$^2$/g to about 1,100 m$^2$/g, about 200 m$^2$/g to about 1,050 m$^2$/g, about 200 m$^2$/g to about 1,000 m$^2$/g, about 200 m$^2$/g to about 900 m$^2$/g, about 200 m$^2$/g to about 850 m$^2$/g, about 200 m$^2$/g to about 800 m$^2$/g, about 200 m$^2$/g to about 700 m$^2$/g, about 200 m$^2$/g to about 600 m$^2$/g, about 200 m$^2$/g to about 550 m$^2$/g, about 200 m$^2$/g to about 500 m$^2$/g, about 200 m$^2$/g to about 450 m$^2$/g, about 200 m$^2$/g to about 400 m$^2$/g, about 200 m$^2$/g to about 300 m$^2$/g, about 500 m$^2$/g to about 2,500 m$^2$/g, about 500 m$^2$/g to about 2,300 m$^2$/g, about 500 m$^2$/g to about 2,200 m$^2$/g, about 500 m$^2$/g to about 2,100 m$^2$/g, about 500 m$^2$/g to about 2,000 m$^2$/g, about 500 m$^2$/g to about 1,900 m$^2$/g, about 500 m$^2$/g to about 1,800 m$^2$/g, about 500 m$^2$/g to about 1,700 m$^2$/g, about 500 m$^2$/g to about 1,600 m$^2$/g, about 500 m$^2$/g to about 1,550 m$^2$/g, about 500 m$^2$/g to about 1,500 m$^2$/g, about 500 m$^2$/g to about 1,450 m$^2$/g, about 500 m²/g to about 1,400 m²/g, about 500 m²/g to about, 300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1,300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica material described herein may have a total surface area of about 200 m²/g to about 2,500 m²/g, particularly about 400 m²/g to about 2,500 m²/g, particularly about 400 m²/g to about 2,000 m²/g, particularly about 500 m²/g to about 2,000 m²/g, or particularly about 400 m²/g to about 1,500 m²/g.

II.G. Pore Volume

The pore volume of the organosilica material made by the methods described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica material can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

In a particular embodiment, the organosilica material can have a pore volume of about 0.1 cm³/g to about 5.0 cm³/g, particularly about 0.1 cm³/g to about 3.0 cm³/g, particularly about 0.2 cm³/g to about 3.0 cm³/g, particularly about 0.2 cm³/g to about 2.5 cm³/g, or particularly about 0.2 cm³/g to about 1.5 cm³/g.

II.H. Additional Metals

In some embodiments, the organosilica material can further comprise at least one catalyst metal incorporated within the pores of the organosilica material. Exemplary catalyst metals can include, but are not limited to, transition metals (Group 3 to Group 12 elements), and particularly, a Group 6 element, a Group 8 element, a Group 9 element, a Group 10 element, a Group 11 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum. Exemplary Group 11 elements can include, but are not limited to, silver and/or copper. Such transition metals may be incorporated within the material, as described below, in the form of metal oxides or metal sulfides, or as dispersed metal particles.

The catalyst metal can be incorporated into the organosilica material by any convenient method, such as by impregnation, by ion exchange, or by complexation to surface sites. The catalyst metal so incorporated may be employed to promote any one of a number of catalytic transformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be silica-alumina, alumina and/or a zeolite, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the catalyst material of the present disclosure is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material of about 100 parts support material to about zero parts binder material; about 99 parts support material to about 1 parts binder material; about 95 parts support material to about 5 parts binder material. Additionally or alternatively, the catalysts described herein typically can comprise, in a composited form, a ratio of support material to binder material ranging from about 90 parts support material to about 10 parts binder material to about 10 parts support material to about 90 parts binder material; about 85 parts support material to about 15 parts binder material to about 15 parts support material to about 85 parts binder material; about 80 parts support material to 20 parts binder material to 20 parts support material to 80 parts binder material, all ratios being by weight, typically from 80:20 to 50:50 support material: binder material, preferably from 65:35 to 35:65. Compositing may be done by conventional means including mulling the materials together followed by extrusion of pelletizing into the desired finished catalyst particles.

In some embodiments, the organosilica material can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the organosilica material can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-11 and/or 13 elements may be present on an exterior and/or interior surface of the organosilica material. For example, one or more of the Group 1, 2 and/or 13 elements may be present in a first layer on the organosilica material and one or more of the Group 6, 8, 9, 10 and/or 11 elements may be present in a second layer, e.g., at least partially atop the Group 1, 2 and/or 13 elements. Additionally or alternatively, only one or more Group 6, 8, 9, 10 and/or 11 elements may present on an exterior and/or interior surface of the organosilica material. These metals may be incorporated as metal oxides or metal sulfides, or as dispersed metal particles. The surface metal(s) can be incorporated into/onto the organosilica material by any convenient method, such as by impregnation, deposition, grafting, co-condensation, by ion exchange, and/or the like.

III. Methods of Making Organosilica Materials

In another embodiment, methods of producing the organosilica material described herein are provided. The method comprises:

(a) providing an aqueous mixture that contains essentially no structure directing agent and/or porogen;

(b) adding at least one compound of Formula $[R^1R^2SiCH_2]_3$ (I) into the aqueous mixture to form a solution, wherein each $R^1$ represents a $C_1$-$C_4$ alkoxy group and $R^2$ represents a $C_1$-$C_4$ alkoxy group or a $C_1$-$C_4$ alkyl group;

(c) adding at least one compound of Formula $[(Z^1O)_xZ^2_{3-x}Si-Z^3-SZ^4]$ (II), wherein, $Z^1$ represents a hydrolysable functional group, $Z^2$ represents a $C_1$-$C_{10}$ alkyl or aryl group, $Z^3$ represents a $C_2$-$C_{11}$ cyclic or linear hydrocarbon, $Z^4$ is either H or $O_3H$; and, x represents any one of integers 1, 2, and 3.

(d) aging the solution to produce a pre-product; and (e) drying the pre-product to obtain an organosilica material which is a polymer comprising at least one independent monomer of Formula (I) as described herein and at least one independent monomer of Formula (II).

III.A. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the structure directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary structure directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4O)_a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly($\alpha$-methyl styrene)). The thermoplastic materials may be linear, branched, hyper-branched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or from about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, about 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, about 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

III.B. Compounds of Formula (I)

The methods provided herein comprise the step of adding at least one compound of Formula $[R^1R^2SiCH_2]_3$ (I) into the aqueous mixture to form a solution, wherein each $R^1$ represents a $C_1$-$C_4$ alkoxy group and each $R^2$ represents a $C_1$-$C_4$ alkoxy group or a $C_1$-$C_4$ alkyl group.

In one embodiment, each $R^1$ can be a $C_1$-$C_3$ alkoxy or methoxy or ethoxy.

Additionally or alternatively, each $R^2$ can be a $C_1$-$C_4$ alkoxy, a $C_1$-$C_3$ alkoxy or methoxy or ethoxy. Additionally or alternatively, each $R^2$ can comprise methyl, ethyl or propyl, such as a methyl or ethyl.

Additionally or alternatively, each $R^1$ can be a $C_1$-$C_2$ alkoxy group and $R^2$ can be a $C_1$-$C_2$ alkoxy group or a $C_1$-$C_2$ alkyl group.

Additionally or alternatively, each $R^1$ can be methoxy or ethoxy and each $R^2$ can be methyl or ethyl.

In a particular embodiment, $R^1$ and $R^2$ can be ethoxy, such that the compound corresponding to Formula (I) can be 1,1,3,3,5,5-hexaethoxy-1,3,5-trisilacyclohexane, $([(EtO)_2SiCH_2]_3)$.

In a particular embodiment, $R^1$ can be ethoxy and $R^2$ can be methyl, such that compound corresponding to Formula (I) can be 1,1,3,3,5,5-hexaethoxy-1,3,5-trisilacyclohexane, $([EtO(CH_3)SiCH_2]_3)$.

In various aspects, more than one compound of Formula (I) (e.g., same or different compound) may be added to the aqueous mixture to form a solution. For example, $[(EtO)_2SiCH_2]_3$ and $[EtO(CH_3)SiCH_2]_3$ may both be added to the aqueous mixture to form a solution.

When more than one compound of Formula (I) is used, the respective compounds may be used in a wide variety of molar ratios. For example, if two compounds of Formula (I) are used, the molar ratio of each compound may vary from 1:99 to 99:1, such as from 10:90 to 90:10. The use of different compounds of Formula (I) allows for tailoring the properties of the organosilica materials made by the processes described herein, as will be further explained in the examples and in the section of this specification describing the properties of the organosilicas made by the present processes.

III.C. Compounds of Formula (II)

In additional embodiments, the methods provided herein can further comprise adding to the aqueous solution a compound of Formula $[(Z^1O)_xZ^2_{3-x}Si—Z^3—SZ^4]$ (II), wherein each $Z^1$ is a hydrolysable functional group, meaning a functional group that is capable of undergoing hydrolysis. $Z^2$ represents a $C_1$-$C_{10}$ alkyl or aryl group; $Z^3$ represents a $C_2$-$C_{11}$ cyclic or linear hydrocarbon; $Z^4$ is either H or $O_3H$, and x represents any one of integers 1, 2, and 3.

In various aspects, $Z^2$ can be a $C_1$-$C_{10}$ alkyl group, a $C_1$-$C_9$ alkyl group, a $C_1$-$C_8$ alkyl group, a $C_1$-$C_7$ alkyl group, a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl.

Additionally or alternatively, $Z^2$ can be a $C_6$-$C_{10}$ aryl group.

Additionally or alternatively, $Z^3$ can be a $C_2$-$C_{12}$ cyclic or linear hydrocarbon.

Additionally or alternatively, $Z^3$ can be a $C_2$-$C_{12}$ alkyl group, a $C_2$-$C_{12}$ alkylene group, a $C_2$-$C_{12}$ nitrogen containing alkyl, a $C_2$-$C_{12}$ nitrogen containing alkylene group, a $C_2$-$C_{12}$ alkenyl group, a $C_2$-$C_{12}$ alkenylene group, a $C_2$-$C_{12}$ alkynyl group, or a $C_2$-$C_{12}$ alkynylene group.

Additionally or alternatively, $Z^3$ can be a $C_6$-$C_{12}$ aryl group, a $C_2$-$C_{12}$ aralkyl group, a $C_4$-$C_{12}$ heterocyclo group, or a $C_4$-$C_{12}$ heterocycloalkyl group.

Additionally or alternatively, $Z^3$ can be a $C_2$-$C_{11}$ cyclic or linear hydrocarbon which has an amine, an ether, a heteroatom, or any combination of amine, ether, or heteroatom incorporated within it.

In a particular embodiment, Formula (II) can be 3-(triethoxysilyl)propane-1-thiol.

III.D. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy. mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato) titanium, di-n-propoxy.bis(acetylacetonato)titanium, di-i-propoxy.bis(acetylacetonato)titanium, di-n-butoxy.bis(acetylacetonato)titanium, di-sec-butoxy.bis(acetylacetonato)titanium, di-t-butoxy.bis(acetylacetonato) titanium, monoethoxy.tris(acetylacetonato)titanium, mono-n-propoxy.tris(acetylacetonato) titanium, mono-i-propoxy.tris(acetylacetonato)titanium, mono-n-butoxy. tris(acetylacetonato)titanium, mono-sec-butoxy.tris(acetylacetonato)titanium, mono-t-butoxy-tris(acetylacetonato)titanium, tetrakis(acetylacetonato) titanium, triethoxy. mono(ethylacetoacetaato)titanium, tri-n-propoxy.mono(ethylacetoacetato)titanium, tri-i-propoxy.mono(ethylacetoacetato) titanium, tri-n-butoxy.mono(ethylacetoacetato) titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoaetato)titanium, mono-i-propoxy.tris(ethylacetoacetato) titanium, mono-n-butoxy.tris(ethylacetoacetato)titanium, mono-sec-butoxy. tris(ethylacetoacetato)titanium, mono-t-butoxy.tris(ethylacetoacetato)titanium, tetrakis(ethylacetoacetato) titanium, mono(acetylacetonato)tris(ethylacetoacetato) titanium, bis(acetylacetonato)bis(ethylacetoacetato)titanium, and tris(acetylacetonato)mono(ethylacetoacetato)titanium; zirconium chelate compounds such as triethoxy.mono(acetylacetonato)zirconium, tri-n-propoxy.mono(acetylacetonato) zirconium, tri-i-propoxy.mono(acetylacetonato)zirconium, tri-n-butoxy.mono(acetylacetonato)zirconium, tri-sec-butoxy.mono(acetylacetonato)zirconium, tri-t-butoxy.mono(acetylacetonato)zirconium, diethoxy.bis(acetylacetonato) zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato) zirconium, mono-n-butoxy.tris(acetylacetonato)zirconium, mono-sec-butoxy. tris(acetylacetonato)zirconium, mono-t-butoxy.tris(acetylacetonato)zirconium, tetrakis(acetylacetonato) zirconium, triethoxy.mono(ethylacetoacetato)zirconium, tri-n-propoxy.mono(ethylacetoacetato)zirconium, tri-i-propoxy.mono(ethylacetoacetato) zirconium, tri-n-butoxy.mono(ethylacetoacetato)zirconium, tri-sec-butoxy.mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato) zirconium, di-sec-butoxy.bis(ethylacetoacetato)zirconium, di-t-butoxy. bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato) zirconium, mono-n-butoxy.tris(ethylacetoacetato)zirconium, mono-sec-butoxy. tris(ethylacetoacetato)zirconium, mono-t-butoxy.tris(ethylacetoacetato)zirconium, tetrakis(ethylacetoacetato) zirconium, mono(acetylacetonato)tris(ethylacetoacetato) zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato) aluminum. Of these, the chelate compounds of titanium or aluminum can be of note, of which the chelate compounds of titanium can be particularly of note. These metal chelate compounds may be used either singly or in combination.

III.E. Molar Ratio

In the methods described herein, a molar ratio of Formula (I):Formula (II) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used.

III.F. Aging the Solution

The solution formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days).

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., at least about 150° C., at least about 175° C., at least about 200° C., at least about 250° C., or about 300° C.

Additionally or alternatively, the solution formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130°

C. to about 300° C., about 130° C. to about 250° C., about 130° C. to about 200° C., about 130° C. to about 175° C., about 130° C. to about 150° C., or about 130° C. to about 140° C.

III.G. Drying the Pre-Product

The methods described herein comprise drying the pre-product (e.g., a gel) to produce an organosilica material.

In some embodiments, the pre-product (e.g., a gel) formed in the method can be dried at a temperature of greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the pre-product (e.g., a gel) formed in the method can be dried at temperature of about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 70° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the pre-product (e.g., a gel) formed in the method can be dried at temperature from about 70° C. to about 200° C.

Additionally or alternatively, the pre-product (e.g., a gel) formed in the method can be dried in a $N_2$ and/or air atmosphere.

III.H. Optional Further Steps

In some embodiments, the method can further comprise calcining the organosilica material to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 400° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 400° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Uses of the Organosilica Materials

The organosilica materials described herein find uses in several areas.

In certain embodiments, the organosilica material described herein can be used as adsorbents or support matrices for separation and/or catalysis processes.

IV.A. Gas Separation Processes

In some cases, the organosilica materials can be used in a gas separation process as provided herein. In various aspects, a gas separation process is provided herein. The gas separation process can comprise contacting a gas mixture containing at least one contaminant with the organosilica material described herein as prepared according to the methods described herein.

In various embodiments, the gas separation process can be achieved by swing adsorption processes, such as pressure swing adsorption (PSA) and temperature swing adsorption (TSA). All swing adsorption processes typically have an adsorption step in which a feed mixture (typically in the gas phase) is flowed over an adsorbent to preferentially adsorb a more readily adsorbed component relative to a less readily adsorbed component. A component may be more readily adsorbed because of kinetic or equilibrium properties of the adsorbent. The adsorbent (e.g., the organosilica material described herein) can typically be contained in a contactor that is part of the swing adsorption unit. The contactor can typically contain an engineered structured adsorbent bed or a particulate adsorbent bed. The bed can contain the adsorbent (e.g., the organosilica material described herein) and other materials such as other adsorbents, mesopore filling materials, and/or inert materials used to mitigated temperature excursions from the heat of adsorption and desorption. Other components in the swing adsorption unit can include, but are not necessarily limited to, valves, piping, tanks, and other contactors. Swing adsorption processes are described in detail in U.S. Pat. Nos. 8,784,533; 8,784,534; 8,858,683; and 8,784,535, each of which are incorporated herein by reference. Examples of processes that can be used herein either separately or in combination are PSA, TSA, pressure temperature swing adsorption (PTSA), partial purge displacement swing adsorption (PPSA), PPTSA, rapid cycle PSA (RCPSA), RCTSA, RCPPSA and RCPTSA.

PSA processes rely on the fact that gases under pressure tend to be adsorbed within the pore structure of the adsorbent materials (e.g., the organosilica material described herein). Typically, the higher the pressure, the greater the amount of targeted gas component that will be adsorbed. When the pressure is reduced, the adsorbed targeted component is typically released, or desorbed. PSA processes can be used to separate gases of a gas mixture, because different gases tend to fill the pores or free volume of the adsorbent to different extents due to either the equilibrium or kinetic properties of the adsorbent. In many important applications, to be described as "equilibrium-controlled" processes, the adsorptive selectivity is primarily based upon differential equilibrium uptake of the first and second components. In another important class of applications, to be described as "kinetic-controlled" processes, the adsorptive selectivity is primarily based upon the differential rates of uptake of the first and second components.

If a gas mixture, such as natural gas, is passed under pressure through a vessel containing a polymeric or microporous adsorbent that is more selective towards carbon dioxide than it is for methane, at least a portion of the carbon dioxide can be selectively adsorbed by the adsorbent, and the gas exiting the vessel can be enriched in methane. When the adsorbent (e.g., the organosilica material described herein) reaches the end of its capacity to adsorb carbon dioxide, it can be regenerated by reducing the pressure, thereby releasing the adsorbed carbon dioxide. The adsorbent is then typically purged and repressurized and ready for another adsorption cycle.

TSA processes also rely on the fact that gases under pressure tend to be adsorbed within the pore structure of the adsorbent materials. When the temperature of the adsorbent (e.g., the organosilica material described herein) is increased, the adsorbed gas is typically released, or desorbed. By cyclically swinging the temperature of adsorbent beds, TSA processes can be used to separate gases in a mixture when used with an adsorbent selective for one or more of the components in a gas mixture. Partial pressure purge displacement (PPSA) swing adsorption (PPSA) processes regenerate the adsorbent with a purge. Rapid cycle (RC) swing adsorption processes complete the adsorption step of a swing adsorption process in a short amount of time. For kinetically selective adsorbents, it can be preferable to use a rapid cycle swing adsorption process. If the cycle time becomes too long, the kinetic selectivity can be lost. These swing adsorption protocols can be performed separately or in combinations. Examples of processes that can be used herein either separately or in combination are PSA, TSA, pressure temperature swing adsorption (PTSA), partial purge displacement swing adsorption (PPSA), PPTSA, rapid cycle PSA (RCPSA), RCTSA, vacuum swing adsorption (VSA), vacuum pressure swing adsorption (VPSA), RCPPSA and RCPTSA.

In PSA processes, a feed gas mixture containing the first and second gas components is separated by cyclic variations of pressure coordinated with cyclic reversals of flow direction in a flow path contacting a fixed bed of the adsorbent material in an adsorber vessel. In the case of TSA or PPSA processes, cyclic variations of temperature and/or partial pressure of the gas components may be coordinated with gas flow through a flow path to perform a separation. The process in any specific PSA application operates at a cyclic frequency characterized by its period, and over a pressure envelope between a first relatively higher pressure and a second relatively lower pressure. Separation in PSA is achieved by coordinating the pressure variations with the flow pattern within the flow path, so that the gas mixture in the flow path is enriched in the second component (owing to preferential adsorptive uptake of the first component in the adsorbent material) when flowing in a first direction in the flow path, while the gas mixture is enriched in the first component (which has been desorbed by the adsorbent material) when flowing in the opposite direction in the flow path. In order to achieve separation performance objectives (i.e. product gas purity, recovery and productivity), process parameters and operating conditions should be designed to achieve a sufficiently high adsorptive selectivity of the first and second components over the adsorbent material, at the cyclic frequency and within the pressure envelope.

Swing adsorption processes can be applied to remove a variety of target gases, also referred to as "contaminant gas" from a wide variety of gas mixtures. Typically, in binary separation systems, the "light component" as utilized herein is taken to be the species or molecular component(s) not preferentially taken up by the adsorbent in the adsorption step of the process. Conversely in such binary systems, the "heavy component" as utilized herein is typically taken to be the species or molecular component(s) preferentially taken up by the adsorbent in the adsorption step of the process. However, in binary separation systems where the component(s) that is(are) preferentially adsorbed has(have) a lower molecular weight than the component(s) that is(are) not preferentially adsorbed, those descriptions may not necessarily correlate as disclosed above.

An example of gas mixture that can be separated in the methods described herein is a gas mixture comprising $CH_4$, such as a natural gas stream. A gas mixture comprising $CH_4$ can contain significant levels of contaminants such as $H_2O$, $H_2S$, $CO_2$, $N_2$, mercaptans, and/or heavy hydrocarbons. Additionally or alternatively, the gas mixture can comprise $NO_x$ and/or $SO_x$ species as contaminants, such as a waste gas stream, a flue gas stream and a wet gas stream. As used herein, the terms "$NO_x$," and "$NO_x$" species refers to the various oxides of nitrogen that may be present in waste gas, such as waste gas from combustion processes. The terms refer to all of the various oxides of nitrogen including, but not limited to, nitric oxide (NO), nitrogen dioxide ($NO_2$), nitrogen peroxide ($N_2O$), nitrogen pentoxide ($N_2O_5$), and mixtures thereof. As used herein, the terms "SOx," and "$SO_x$ species," refers to the various oxides of sulfur that may be present in waste gas, such as waste gas from combustion processes. The terms refer to all of the various oxides of sulfur including, but not limited to, SO, $SO_2$, $SO_3$, $SO_4$, $S_7O_2$ and $S_6O_2$. Thus, examples of contaminants include, but are not limited to $H_2O$, $H_2S$, $CO_2$, $N_2$, mercaptans, heavy hydrocarbons, $NO_x$ and/or $SO_x$ species. In particular, the gas mixture may comprise $CH_4$ and the at least one contaminant is $CO_2$ and/or $H_2S$.

Another example of a gas mixture that can be separated in the methods described herein is a gas mixture comprising nitrogen and carbon dioxide, such as exhaust gas or flue gas. Such gases can contain significant levels of $CO_2$, $N_2$, and $H_2O$. Separation of $CO_2$ from $N_2$ is imperative for carbon capture and sequestration purposes.

In various aspects, a process for selectively separating a contaminant from a feed gas mixture is provided herein. The process may comprise: a) contacting the feed gas mixture under sorption conditions with the organosilica material described herein; b) adsorbing the contaminant into/onto the organosilica material described herein; c) subjecting the organosilica material described herein to desorption conditions by which at least a portion of the sorbed contaminant is desorbed; and d) retrieving a contaminant-rich product stream that has a higher mol % of contaminant than the feed gas mixture. The feed gas mixture may be any of the gas mixtures described above. Particularly, the feed gas mixture may comprise $CH_4$. The contaminant may be any of the contaminants described above, e.g., $CO_2$, $H_2S$, etc.

It may be desirable to operate with a multiplicity of structured adsorbent beds, with several coupled in a heating/cooling operation and others involved in adsorption (and/or desorption). In such an operation, the adsorbent bed can be substantially cooled by a circulating heat transfer medium before it is switched into service for adsorption. One advantage of such an operation can be that the thermal energy used to swing the bed is retained in the heat transfer medium. If adsorption were to proceed simultaneously with cooling, then a substantial part of the heat in the bed could be lost to the adsorbate-free feed, and a higher heat load could be needed to restore the high temperature of the heat transfer medium. It may also be desirable to use a rotary adsorbent bed, which provides similar benefits to the multiple adsorbent beds described above.

Adsorptive kinetic separation (AKS) processes, as described above, are useful for development and production of hydrocarbons, such as gas and oil processing. Particularly, as described in U.S. Patent Application Publication No. 2013/032716, which is herein incorporated by reference in its entirety, the AKS processes described herein can use one or more kinetic swing adsorption process, such as pressure swing adsorption (PSA), thermal swing adsorption (TSA), and partial pressure swing or displacement purge adsorption (PPSA), including combinations of these processes; each swing adsorption process may be utilized with rapid cycles, such as using one or more rapid cycle pressure swing adsorption (RCPSA) units, with one or more rapid cycle temperature swing adsorption (RCTSA) units or with one or more rapid cycle partial pressure swing adsorption (RCPPSA) units; exemplary kinetic swing adsorption processes are described in U.S. Pat. Nos. 7,959,720; 8,545,602; 8,529,663; 8,444,750; 8,529,662, 8,784,533, 8,784,534, 8,784,535, and 9,034,079, which are each herein incorporated by reference in its entirety. The provided processes, can be useful for rapid, large scale, efficient separation of a variety of target gases from gas mixtures.

The provided processes and apparatuses may be used to prepare natural gas products by removing contaminants. The provided processes and apparatuses can be useful for preparing gaseous feed streams for use in utilities, including separation applications such as dew point control, sweetening/detoxification, corrosion protection/control, dehydration, heating value, conditioning, and purification. Examples of utilities that utilize one or more separation applications can include generation of fuel gas, seal gas, non-potable water, blanket gas, instrument and control gas, refrigerant, inert gas, and hydrocarbon recovery. Exemplary "not to exceed" product (or "target") acid gas removal specifications can include: (a) 2 vol. % $CO_2$, 4 ppm $H_2S$; (b) 50 ppm $CO_2$, 4 ppm $H_2S$; or (c) 1.5 vol. % $CO_2$, 2 ppm $H_2S$.

The provided processes and apparatuses may also be used to remove acid gas from hydrocarbon streams. Acid gas removal technology becomes increasingly important as remaining gas reserves exhibit higher concentrations of acid (sour) gas resources. Hydrocarbon feed streams can vary widely in amount of acid gas, such as from several parts per million to 90 vol. %. Non-limiting examples of acid gas concentrations from exemplary gas reserves can include concentrations of at least: (a) 1 vol. % $H_2S$, 5 vol. % $CO_2$; (b) 1 vol. % $H_2S$, 15 vol. % $CO_2$; (c) 1 vol. % $H_2S$, 60 vol. % $CO_2$; (d) 15 vol. % $H_2S$, 15 vol. % $CO_2$; or (e) 15 vol. % $H_2S$, 30 vol. % $CO_2$.

As described above, the organosilica material is a high surface area material and is capable of anchoring a high loading of transition metal ions, such as $Ag^+$, which can be very effective in accomplishing olefin/paraffin separation from petrochemical feeds. Relatedly, because of its ability to anchor a high loading of transition metal ions, the disclosed organosilica materials can be used as a catalyst support for metallic nanoparticles.

One or more of the following may be utilized with the processes and apparatuses provided herein, to prepare a desirable product stream, while maintaining relatively high hydrocarbon recovery:

(a) removing acid gas with RCTSA using advanced cycles and purges as described in U.S. Pat. Nos. 8,784,533 and 9,005,561, which are together incorporated by reference herein in their entirety;

(b) using a mesopore filler to reduce the amount of trapped methane in the adsorbent bed and increase the overall hydrocarbon recovery, as described in U.S. Pat. Nos. 7,959,720; 8,444,750; and 8,529,663, each of which is herein incorporated by reference in its entirety;

(c) depressurizing one or more RCTSA units in multiple steps to intermediate pressures so that the acid gas exhaust can be captured at a higher average pressure, thereby decreasing the compression required for acid gas injection; pressure levels for the intermediate depressurization steps may be matched to the interstage pressures of the acid gas compressor to optimize the overall compression system;

(d) using exhaust or recycle streams to minimize processing and hydrocarbon losses, such as using exhaust streams from one or more RCTSA units as fuel gas instead of re-injecting or venting;

(e) using multiple adsorbent particles in a single bed to remove trace amounts of first contaminants, such as $H_2S$, before removal of a second contaminant, such as $CO_2$; such segmented beds may provide rigorous acid gas removal down to ppm levels with RCTSA units with minimal purge flow rates;

(f) using feed compression before one or more RCTSA units to achieve a desired product purity;

(g) contemporaneous removal of non-acid gas contaminants such as mercaptans, carbonyl sulfide, benzene, toluene, ortho-, meta-, and para-xylene; selection processes and materials to accomplish the same;

(h) selecting a cycle time and cycle steps based on adsorbent material kinetics; and (i) using a process and apparatus that uses, among other equipment, two RCTSA units in series, wherein the first RCTSA unit cleans a feed stream down to a desired product purity and the second RCTSA unit cleans the exhaust from the first unit to capture methane and maintain high hydrocarbon recovery; use of this series design may reduce the need for a mesopore filler.

(j) oxidizing the thiol group of the thiol terminated mesoporous oganosilica material of the present disclosure to produce a mesoporous organosilica material exhibiting terminal sulfonic acids which can be used in acid catalysis and as a polar sorbent for crude feeds.

IV.B. Aromatic Hydrogenation Process

The organosilica materials made according to the methods described herein can be used as support materials in hydrogenation catalysts. In particular, the hydrogenation catalyst can comprise the organosilica materials as a support material where the organosilica material has at least one catalyst metal incorporated on the pore surface. The at least one catalyst metal may be a transition metal, e.g., Ag, Pt, Pd, Ir, Rh, Ru or a combination thereof. The hydrogenation catalyst can further comprise a binder such as, but not limited to, active and inactive materials, inorganic materials, clays, ceramics, activated carbon, alumina, silica, silica-alumina, titania, zirconia, niobium oxide, tantalum oxide, or a combination thereof, particularly, silica-alumina, alumina, titania, or zirconia. These hydrogenation catalysts can be used for both hydrogenation and aromatic saturation of a feedstream.

In various embodiments, the hydrogenation process can be achieved by contacting a hydrocarbon feedstream comprising aromatics with a hydrogenation catalyst described herein in the presence of a hydrogen-containing treat gas in a first reaction stage operated under effective aromatics hydrogenation conditions to produce a reaction product with reduced aromatics content.

Hydrogen-containing treat gases suitable for use in a hydrogenation process can be comprised of substantially pure hydrogen or can be mixtures of other components typically found in refinery hydrogen streams. It is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results. It is most preferred that the hydrogen-containing stream be substantially pure hydrogen.

Feedstreams suitable for hydrogenation by the hydrogenation catalyst described herein include any conventional hydrocarbon feedstreams where hydrogenation or aromatic saturation is desirable. Typically, an input feed for an aromatic saturation process can be generated as a product or side-product from a previous type of hydroprocessing, such as hydrocracking for fuels or lubricant base stock production. A wide range of petroleum and chemical feedstocks can be hydroprocessed. Such feedstreams can include hydrocarbon fluids, diesel, kerosene, lubricating oil feedstreams, heavy coker gasoil, de-asphalted oil (DAO), FCC main column bottom (MCB), steam cracker tar. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 650-1100° F. (343-593° C.). Diesel boiling range feedstreams include feedstreams which boil in the range of 480-660° F. (249-349° C.). Kerosene boiling range feedstreams include feedstreams which boil in the range of 350-617° F. (177-325° C.).

Hydrocarbon feedstreams suitable for use herein also contain aromatics and nitrogen- and sulfur-contaminants. Feedstreams containing up to 0.2 wt. % of nitrogen, based on the feedstream, up to 3.0 wt. % of sulfur, and up to 50 wt. % aromatics can be used in the present process. In various embodiments, the sulfur content of the feedstreams can be below about 500 wppm, or below about 300 wppm, or below about 200 wppm, or below about 100 wppm, or below about 50 wppm, or below about 15 wppm. The pressure used during an aromatic hydrogenation process can be modified based on the expected sulfur content in a feedstream. Feeds having a high wax content typically have high viscosity indexes of up to 200 or more. Sulfur and nitrogen contents may be measured by standard ASTM methods D2622 (sulfur), and D5453 and/or D4629 (nitrogen), respectively.

Effective hydrogenation conditions may be considered to be those conditions under which at least a portion of the aromatics present in the hydrocarbon feedstream are saturated, preferably at least about 50 wt. % of the aromatics are saturated, more preferably greater than about 75 wt. %. Effective hydrogenation conditions can include temperatures of from 150° C. to 400° C., a hydrogen partial pressure of from 740 to 20786 kPa (100 to 3000 psig), a space velocity of from 0.1 to 10 liquid hourly space velocity (LHSV), and a hydrogen to feed ratio of from 89 to 1780 $m^3/m^3$ (500 to 10000 scf/B).

Additionally or alternatively, effective hydrogenation conditions may be conditions effective at removing at least a portion of the nitrogen and organically bound sulfur contaminants and hydrogenating at least a portion of said aromatics, thus producing at least a liquid lube boiling range product having a lower concentration of aromatics and nitrogen and organically bound sulfur contaminants than the lube boiling range feedstream.

Additionally or alternatively, effective hydrogenation conditions may be conditions effective at removing at least a portion of the nitrogen and organically bound sulfur contaminants and hydrogenating at least a portion of said aromatics, thus producing at least a liquid diesel boiling range product having a lower concentration of aromatics and nitrogen and organically bound sulfur contaminants than the diesel boiling range feedstream.

As stated above, in some instances, the hydrocarbon feedstream (e.g., lube oil boiling range) may be hydrotreated to reduce the sulfur contaminants to below about 500 wppm, particularly below about 300 wppm, particularly below about 200 wppm or particularly below about 100 wppm. In such an embodiment, the process may comprise at least two reaction stages, the first reaction state containing a hydrotreating catalyst operated under effective hydrotreating conditions, and the second containing a hydrogenation catalyst has described herein operated under effective hydrogenation conditions as described above. Therefore, in such an embodiment, the hydrocarbon feedstream can be first contacted with a hydrotreating catalyst in the presence of a hydrogen-containing treat gas in a first reaction stage operated under effective hydrotreating conditions in order to reduce the sulfur content of the feedstream to within the above-described range. Thus, the term "hydrotreating" as used herein refers to processes wherein a hydrogen-containing treat gas is used in the presence of a suitable catalyst that is active for the removal of heteroatoms, such as sulfur, and nitrogen. Suitable hydrotreating catalysts include at least one catalyst metal comprised of at least one Group 8 metal, preferably Fe, Co and Ni, more preferably Co and/or Ni, and most preferably Ni; and at least one Group 6 metal, preferably Mo and W, more preferably Mo, on a high surface area support material of an organosilica material described herein, preferably organosilica materials including an aluminum component. The aluminum component may be grafted on the surface of the organosilica material, for example prior to impregnating the catalyst metal, or the aluminum component may be provided within the aqueous mixture used to form the organosilica material. Additionally or alternatively, more than one type of hydrotreating catalyst can be used in the same reaction vessel. The Group 8 metal may typically be present in an amount ranging from about 2 to 20 wt. %, preferably from about 4 to 12 wt. %. The Group 6 metal can typically be present in an amount ranging from about 5 to 50 wt. %, preferably from about 10 to 40 wt. %, and more preferably from about 20 to 30 wt. %. All metals weight percents are "on support" as described above.

Effective hydrotreating conditions may be considered to be those conditions that can effectively reduce the sulfur content of the feedstream (e.g., lube oil boiling range) to within the above-described ranges. Typical effective hydrotreating conditions can include temperatures ranging from about 150° C. to about 425° C., preferably about 200° C. to about 370° C., more preferably about 230° C. to about 350° C. Typical weight hourly space velocities ("WHSV") may range from about 0.1 to about 20 hr$^{-1}$, preferably from about 0.5 to about 5 hr$^{-1}$. Any effective pressure can be utilized, and pressures can typically range from about 4 to about 70 atmospheres (405 to 7093 kPa), preferably 10 to 40 atmospheres (1013 to 4053 kPa). In a particular embodiment, said effective hydrotreating conditions may be conditions effective at removing at least a portion of said organically bound sulfur contaminants and hydrogenating at least a portion of said aromatics, thus producing at least a reaction product (e.g., liquid lube oil boiling range product) having a lower concentration of aromatics and organically bound sulfur contaminants than the lube oil boiling range feedstream.

The contacting of the hydrocarbon feedstream with the hydrotreating catalyst may produce a reaction product comprising at least a vapor product and a liquid product. The vapor product may typically comprise gaseous reaction products, such as H$_2$S, and the liquid reaction product may typically comprise a liquid hydrocarbon having a reduced level of nitrogen and sulfur contaminants. The total reaction product can be passed directly into the second reaction stage, but it may be preferred that the gaseous and liquid reaction products be separated, and the liquid reaction product conducted to the second reaction stage. Thus, in one embodiment, the vapor product and the liquid product may be separated, and the liquid product may be conducted to the second reaction stage. The method of separating the vapor product from the liquid product can be accomplished by any means known to be effective at separating gaseous and liquid reaction products. For example, a stripping tower or reaction zone can be used to separate the vapor product from the liquid product (e.g., liquid lube oil boiling range product). The liquid product thus conducted to the second reaction stage can have a sulfur concentration within the range of about 500 wppm, particularly below about 300 wppm, or particularly below about 200 wppm or particularly below about 100 wppm.

In still other embodiments, the hydrogenation catalysts described herein can be used in integrated hydroprocessing methods. In addition to the hydrofinishing and/or aromatic hydrogenation/saturation processes involving the hydrogenation catalyst described herein, an integrated hydroprocessing method can also include various combinations of hydrotreating, hydrocracking, catalytic dewaxing (such as hydrodewaxing), and/or solvent dewaxing. The scheme of hydrotreating followed by hydrofinishing described above represents one type of integrated process flow. Another integrated processing example is to have a dewaxing step, either catalytic dewaxing or solvent dewaxing, followed by hydroprocessing with the hydrogenation catalysts described herein. Still another example is a process scheme involving hydrotreating, dewaxing (catalytic or solvent), and then hydroprocessing with the hydrogenation catalysts described herein. Yet another example is hydroprocessing with the hydrogenation catalysts described herein followed by dewaxing (catalytic or solvent). Alternatively, multiple hydrofinishing and/or aromatic hydrogenation steps can be employed with hydrotreatment, hydrocracking, or dewaxing steps. An example of such a process flow is hydrofinishing, dewaxing (catalytic or solvent), and then hydrofinishing again, where at least one of the hydrofinishing steps may use hydrogenation catalysts described herein. For processes involving catalytic dewaxing, effective catalytic dewaxing conditions can include temperatures of from 150° C. to 400° C., preferably 250° C. to 350° C., pressures of from 791 to 20786 kPa (100 to 3000 psig), preferably 1480 to 17338 kPa (200 to 2500 psig), liquid hourly space velocities of from 0.1 to 10 hr$^{-1}$, preferably 0.1 to 5 hr$^{-1}$ and hydrogen treat gas rates from 45 to 1780 m$^3$/m$^3$ (250 to 10000 scf/B), preferably 89 to 890 m$^3$/m$^3$ (500 to 5000 scf/B). Any suitable dewaxing catalyst may be used.

In embodiments where the product of an aromatic saturation process will be a lubricant base oil, the input feed should also have suitable lubricant base oil properties. For example, an input feed intended for use as a Group I or Group II base oil can have a viscosity index (VI) of at least about 80, preferably at least about 90 or at least about 95. An input feed intended for use as a Group I+ base oil can have a VI of at least about 100, while an input feed intended for use as a Group II+ base oil can have a VI of at least 110. The viscosity of the input feed can be at least 2 cSt at 100° C., or at least 4 cSt at 100° C., or at least 6 cSt at 100° C.

V. Further Embodiments

Embodiment 1

An organosilica material comprising a copolymer of at least one monomer of Formula [R$^1$R$^2$SiCH$_2$]$_3$ (I), wherein, R$^1$ represents a C$_1$-C$_4$ alkoxy group; and R$^2$ is a C$_1$-C$_4$ alkoxy group or a C$_1$-C$_4$ alkyl group; and at least one other monomer of Formula [(Z$^1$O)$_x$Z$^2$$_{3-x}$Si—Z$^3$—SZ$^4$] (II), wherein, Z$^1$ represents a hydrolysable functional group; Z$^2$ represents a C$_1$-C$_{10}$ alkyl or aryl group; Z$^3$ represents a C$_2$-C$_{11}$ cyclic or linear hydrocarbon; Z$^4$ is either H or O$_3$H; and x represents any one of integers 1, 2, and 3.

Embodiment 2

The organosilica material of embodiment 1, wherein Z$^3$ has incorporated within the C$_2$-C$_{11}$ cyclic or linear hydrocarbon (i) an amine, (ii) an ether, (iii) a heteroatom, or (iv) a combination of any of (i), (ii), and (iii), provided that Si and S remain bonded to a carbon atom.

Embodiment 3

The organosilica material of any of the previous embodiments, further comprising a catalyst metal.

Embodiment 4

The organosilica material of embodiment 3, wherein the catalyst metal is one of a transition metal, a metal oxide, and a metal sulfide.

Embodiment 5

The organosilica material of embodiment 3 or 4, wherein the catalyst metal is incorporated as dispersed metal particles.

Embodiment 6

The organosilica material of any of embodiments 3-5, wherein the catalyst metal comprises silver.

Embodiment 7

A method for separation of olefins from paraffins comprising: contacting a hydrocarbon stream comprising olefins and paraffins with an adsorbent bed to produce an paraffins rich stream, wherein the adsorbent bed comprises: (i) an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3; and (ii) at least one catalyst metal.

Embodiment 8

The method of embodiment 7 wherein the at least one catalyst metal is silver or copper.

Embodiment 9

A hydrogenation process for a hydrocarbon feedstream comprising: contacting a hydrocarbon feedstream with a hydrogenation catalyst in the presence of a hydrogen-containing treat gas in a reaction stage operated under effective hydrogenation conditions, wherein the hydrogenation catalyst comprises: (i) an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3; and (ii) at least one catalyst metal.

Embodiment 10

A method for separation of polar organic compounds from a hydrocarbon feed comprising: contacting the hydrocarbon stream comprising polar organic compounds with an adsorbent bed to produce a hydrocarbon stream with a reduced concentration of polar organic compounds, wherein the adsorbent bed comprises an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3.

EXAMPLES

General Methods

Small Angle X-Ray Diffraction Analysis

X-ray powder diffraction (XRD) patterns were collected on a PANalytical X'pert diffractometer equipped with an accessory for low angle measurements. XRD analyses were recorded using the Cu K$\alpha$ (=1.5405980 Å) line in the 2$\theta$ range from 0.5 to 100 with a step size of 0.0167° and a counting time of 1.2 s.

Solid-State NMR Measurements

The solid-state NMR spectra were recorded on a Varian InfinityPlus-500 spectrometer operating at 11.74T, corresponding to $^1H$, $^{13}C$, and $^{29}Si$ Larmor frequencies of 499.2, 125.5, and 99.2 MHz, respectively. The spinning speeds used were 40 kHz ($^1H$, $^{13}C$) and 5 kHz ($^{29}Si$), respectively. The $^{29}Si$ MAS NMR spectra were acquired with a 4.0 μs 90° pulse and a 60 s recycle delay, with proton decoupling during data acquisition, using a 7.5 mm MAS probe head. The $^1H$ MAS NMR and $^{13}C$ CPMAS NMR spectra were recorded using a 1.6 mm Fast-MAS probe head using 40 kHz spinning. The $^1H$ NMR spectra were obtained using a 2 μs 90° pulse and a 5 s recycle delay. The $^{13}C$ CPMAS NMR used a 2 μs 90° pulse, 2.5 ms $^1H$—$^{13}C$ cross-polarization (CP) contact time, and a recycle delay of 3 s, with proton decoupling during data acquisition. The chemical shifts are referenced with respect to an external tetramethyl silane ($\delta_H$=0.0 ppm, $\delta_C$=0.0 ppm, $\delta_{Si}$=0.0 ppm) and all of the NMR spectra were recorded at room temperature using air for spinning.

Thermal Gravimetric Analysis (TGA)

Thermal stability results were recorded on Q5000 TGA. Ramp rate was 5° C./min, temperature range was from 25° C. to 800° C. All the samples were tested in both air and nitrogen.

$CO_2$ Adsorption

The work was done with a Quantchrome Autosorb AS-iQ2. All the samples were pre-treated at 120° C. in vacuum for 3 hours before collecting the $CO_2$ isotherm at different temperatures.

Nitrogen Porosimetry

The nitrogen adsorption/desorption analyses was performed with different instruments, e.g. TriStar 3000, TriStar II 3020 and a Quantachrome Autosorb AS-1C. All the samples were pre-treated at 120° C. in vacuum for 4 hours before collecting the $N_2$ isotherm. The analysis program calculated the experimental data and reported BET surface area (total surface area), microporous surface area, total pore volume, pore volume for micropores, average pore diameter (or radius), etc.

Scanning Electron Microscopy (SEM)

Scanning electron microscopy was conducted on a Hitachi 4800 scanning electron microscope using an accelerating voltage between 1 and 20 keV. All the samples were prepared by supporting dried powders on conductive carbon adhesive tape.

Energy Dispersive X-ray Spectroscopy (EDX)

Energy dispersive X-ray spectroscopy was conducted in the Hitachi 4800 SEM while at accelerating voltages of 20 keV.

Transmission Electron Microscopy (TEM)

Transmission Electron Micrograph samples were prepared by grinding of the sample in an agate mortar and pestle and dusting the fines onto a 200 mesh, holey carbon-coated copper grid. The samples were transferred into a Philips CM200F TEM/STEM and examined in the bright field TEM imaging mode at an accelerating voltage of 200 kV. Digital images were collected from representative regions of the materials using a Gatan CCD camera and Gatan Digital Micrograph software.

Example 1

Synthesis of Mesoporous Organosilicate Material with Terminal Thiol Groups (MOS—SH)

3.9 mL of 1,1,3,3,5,5-hexaethoxy-1,3,5-trisilacyclohexane ([(EtO)$_2$SiCH$_2$]$_3$) and 1.47 mL of 3-(triethoxysilyl)propane-1-thiol was added to 90 mL of 7.25 M aqueous ammonium hydroxide (1:1 dilution of concentrated NH$_4$OH with water). The solution was allowed to stir overnight at room temperature (about 20-25° C.) until a homogeneous solution resulted. It is possible that some precipitation may occur. In such cases, the solution was filtered through celite prior to proceeding to the next steps.

The solution was then added to a Parr reactor and heated at 90° C. overnight, which resulted in the formation of gel. The gel was then heated in a vacuum oven at 90° C. until dryness. This produced a sample a clear solid, which was converted to white powder after grinding (hereinafter referred to as Sample 1). No structure directing agent or porogen were used in this preparation. The resulting MOS—SH was analyzed via SEM and EDX.

SEM Imaging

SEM was performed on Sample 1 and is shown in FIG. 1.

EDX Analysis

Figure 2A:
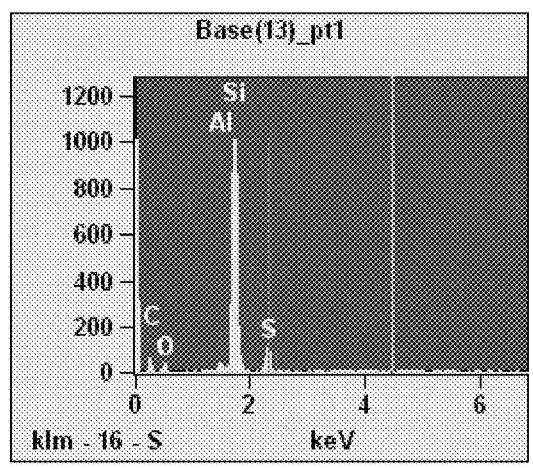
FIGS. 2A, 2B, and 2C are energy dispersive X-ray (EDX) spectroscopy plots of points 1, 2, and 3 of the composition shown in FIG. 1.
Figure 2B:
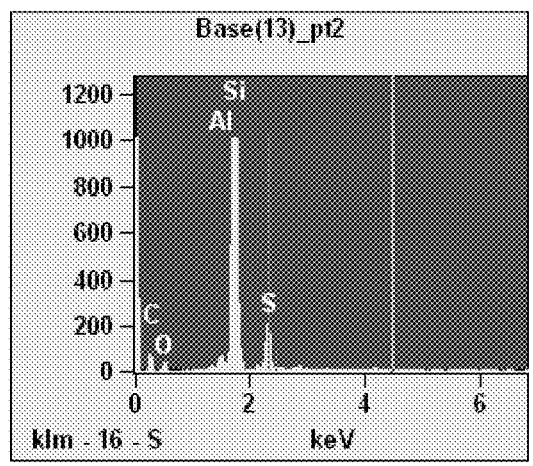
Figure 2C:
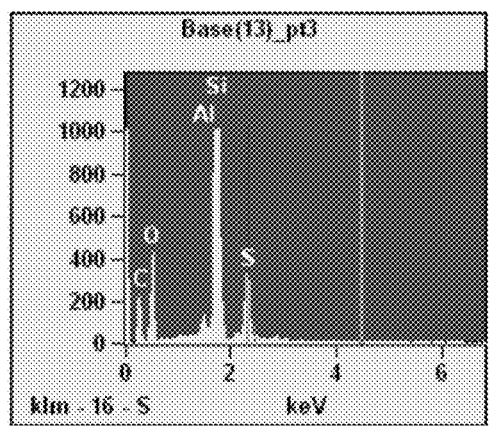

EDX analysis was performed on Sample 1 at points 1, 2 and 3 of the SEM image. The resulting spectroscopy characteristics are shown in FIGS. 2A, 2B, and 2C (at points 1, 2, and 3 of FIG. 1, respectively). The aluminum content is indicative of the test equipment and is not contained within Sample 1 itself. As can be seen in Table 1, the sulfur is incorporated relatively homogeneously within the material, which is evidenced by the nearly uniform sulfur to silica ratio of about 0.16-0.17.

TABLE 1

|  | C—K | O—K | Al—K | Si—K | S—K |
|---|---|---|---|---|---|
| Base(13)_pt1 | 44.19 | 12.64 | 0.66 | 36.64 | 5.88 |
| Base(13)_pt2 | 43.31 | 8.78 | 0.70 | 40.28 | 6.93 |
| Base(13)_pt3 | 39.72 | 27.14 | 0.61 | 28.03 | 4.50 |

TGA Analysis

Figure 3A:
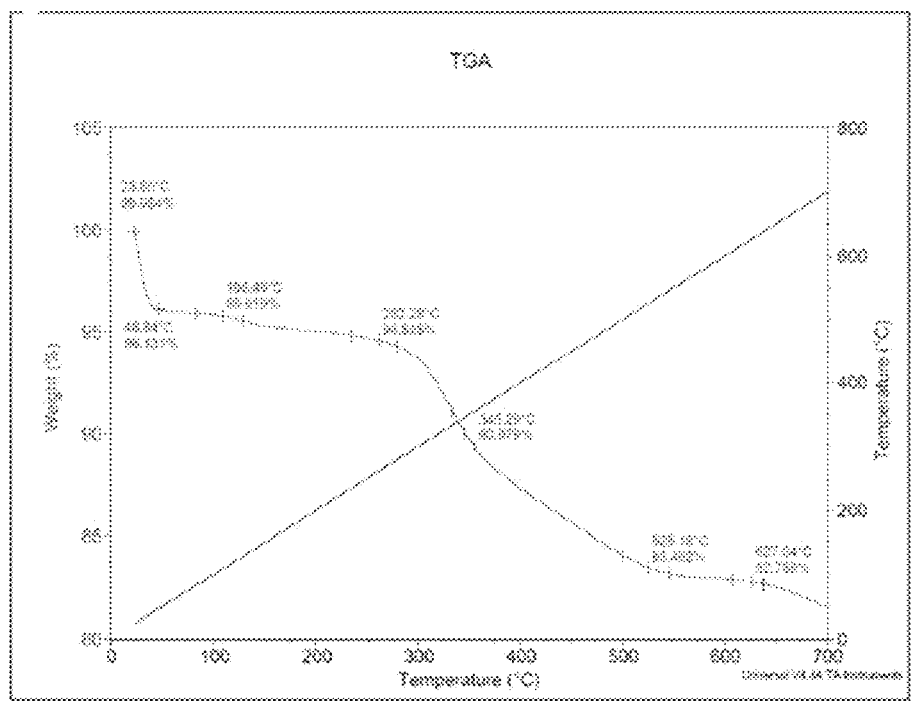
FIG. 3A is a thermogravimetric analysis (TGA) of an exemplary composition disclosed herein.

TGA weight loss studies were performed on Sample 1 in nitrogen. FIG. 3A displays the TGA data for Sample 1 in nitrogen.

Nitrogen Adsorption/Desorption Analysis

Figure 4A:
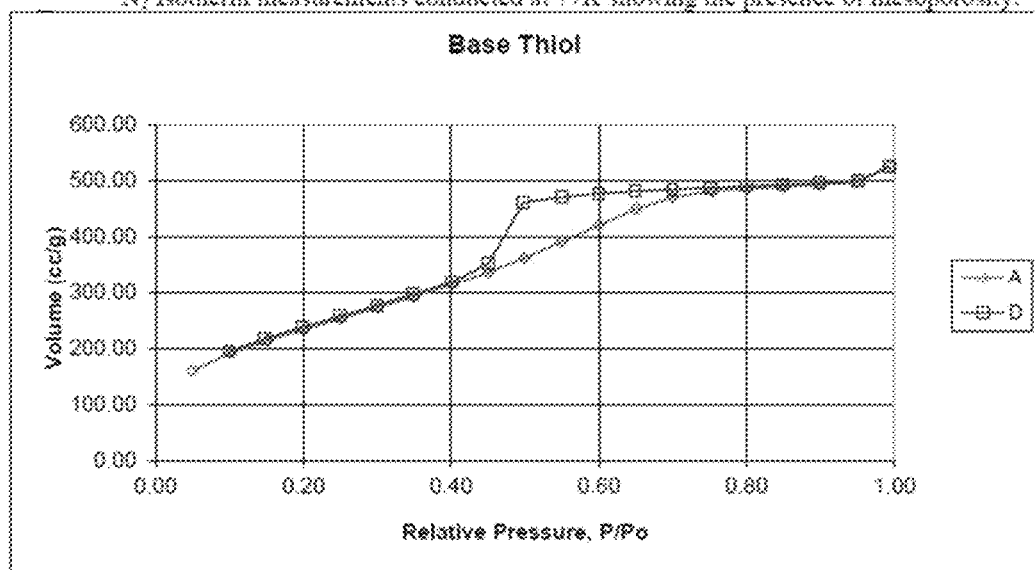
FIG. 4A is a nitrogen adsorption/desorption analysis of an exemplary composition disclosed herein.

Nitrogen adsorption/desorption analysis was performed on Sample 1, and adsorption (line "A") and desorption (line "D") isotherm measurements conducted at 77K are provided in FIG. 4A. The initial adsorption at low (<0.3 P/P$_0$) pressures indicate the high surface area of this material (>700 m$^2$/g) while the large divergence in the adsorption and desorption branches between relative pressures of about 0.43 to about 0.7 indicates the presence of mesoporosity typical of these template-free silica materials.

Example 2

Attachment of Transition Metal Cations to MOS—SH

One gram of MOS—SH made in a similar manner as Sample 1 was suspended in a vessel containing 50 mL of water. To this suspension, 0.5 grams of silver nitrate was added. The vessel was wrapped in aluminum foil, then gently agitated and allowed to sit for about 16 hours. The quiescent solution was then filtered through a porous paper filter. The resulting silver-modified MOS—SH (MOS—SH—Ag) particles (hereinafter referred to as Sample 2) were washed with about 250 mL of water followed by methanol to remove excess AgNO$_3$ and excess bulk water.

Allowing Sample 2 to sit under vacuum at slightly elevated temperatures, about 70° C., in the presence of light results in the formation of a red-color consistent with the formation of small metal nanoparticles. Sample 2 was then heated to 250° C. under nitrogen for 4 hours, which resulted in black colored specks indicating larger metal nanoparticles. Indeed TEM analysis indicated that after this mild heating treatment, the particles ripened from about 1.9 nm to 2-5 nm.

Sample 2 was analyzed via TEM and EDX.

TEM Imaging

Figure 5A:
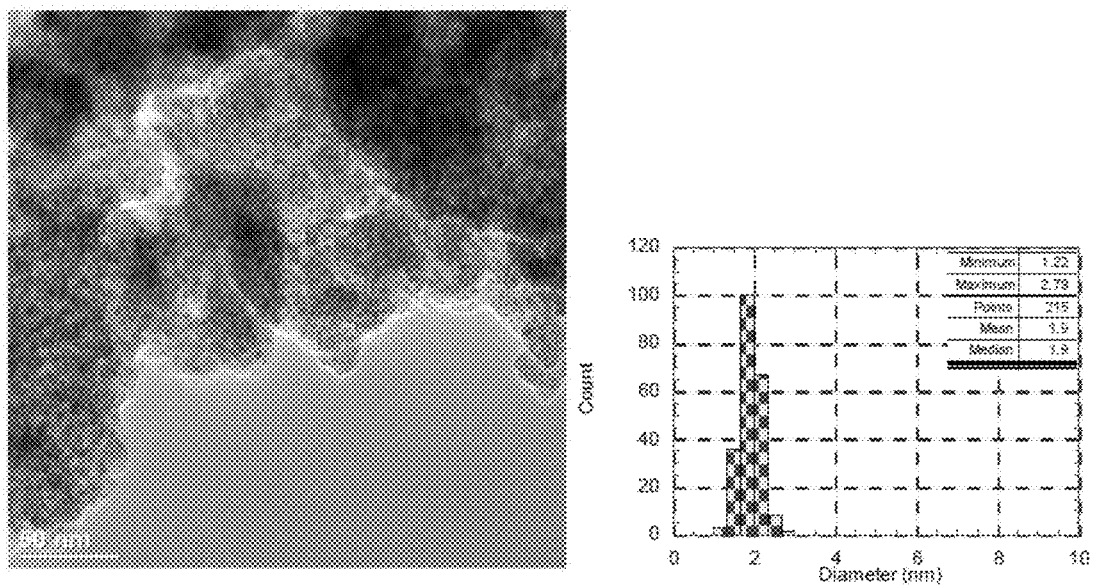
FIGS. 5A and 5B are transmission electron microscopy (TEM) images of an exemplary composition disclosed herein with incorporated transition metal nanoparticles ($Ag^+$) at 70° C. and 250° C. respectively.
Figure 5B:
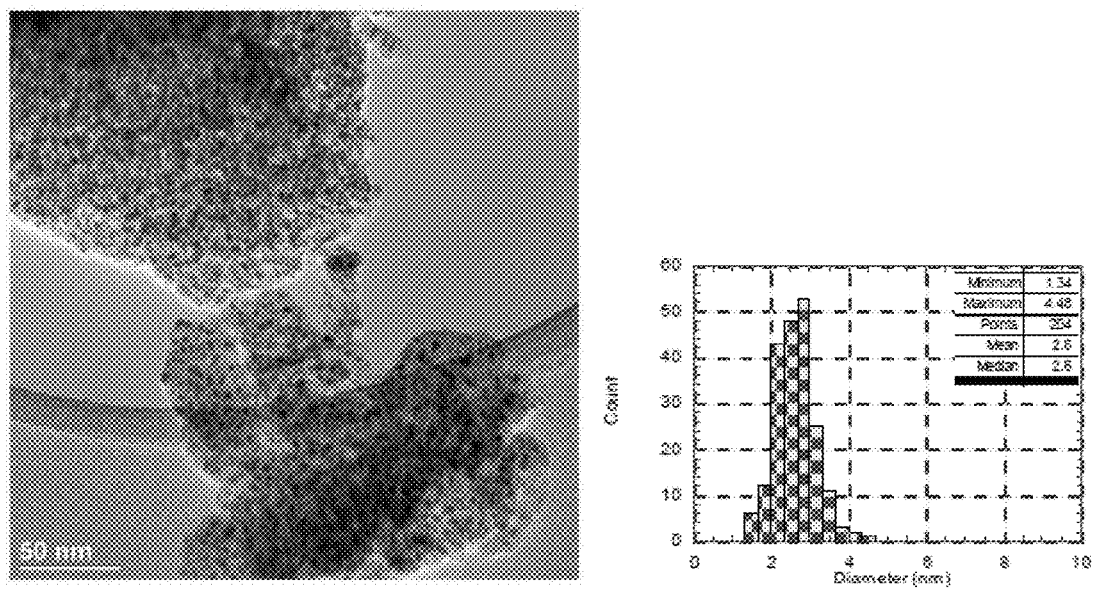

TEM was performed on Sample 2 after aging in a vacuum at 70° C. with exposure to ambient light (FIG. 5A) and after calcination at 250° C. under nitrogen (FIG. 5B). Accompanying FIGS. 5A and 5B are tables showing the mean silver nanoparticle size. Of note, the calcined sample, while showing a larger mean silver nanoparticle diameter (2.6 nm as compared 1.9 nm), still shows well-dispersed silver nanoparticles throughout the Sample 2. The presence of sulfur on the surface of the mesoporous silica, strongly adheres to the silver particles and is thought to inhibit particle mobility resulting in resistance to agglomeration.

EDX Analysis

Figure 6A:
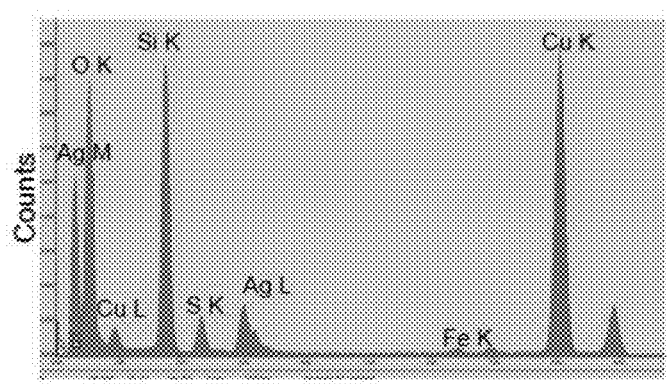
FIGS. 6A and 6B are EDX spectroscopy plots of an exemplary composition disclosed herein with incorporated transition metal nanoparticles ($Ag^+$) at 70° C. and 250° C., respectively.
Figure 6B:
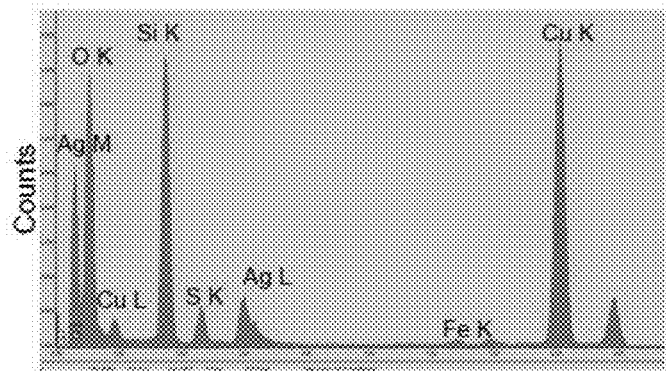

EDX analysis was performed on Sample 2 after aging in a vacuum at 70° C. with exposure to ambient light (FIG. 6A) and after calcination at 250° C. under nitrogen (FIG. 6B). The copper content is indicative of the test equipment and is not contained within Sample 2 itself. This analysis indicates the presence of the both silver and sulfur species and gives an indication of the chemical composition of the material.

TGA Analysis

Figure 3B:
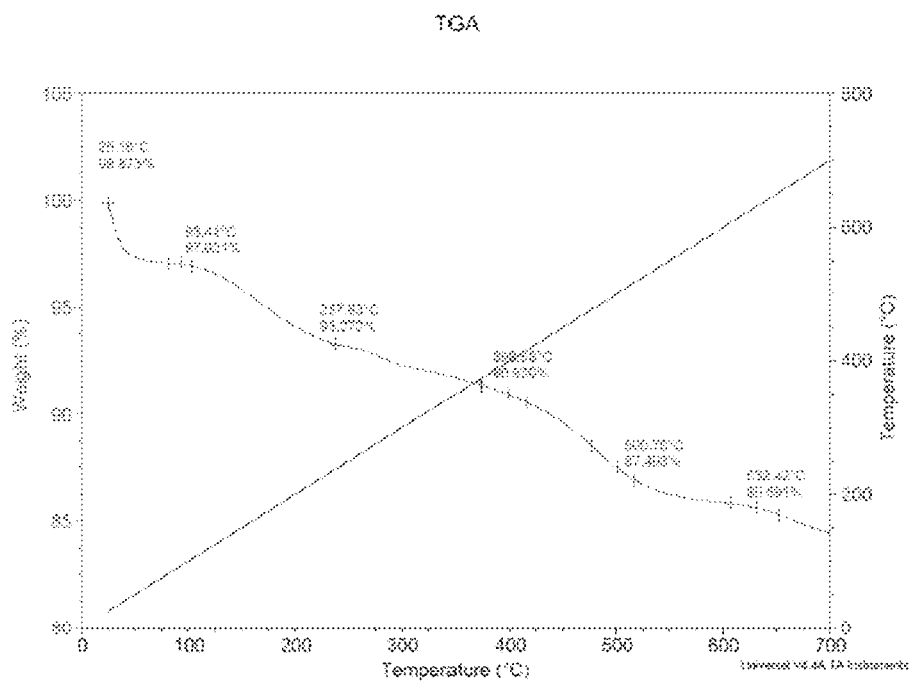
FIG. 3B is a TGA of an exemplary composition disclosed herein with incorporated transition metal nanoparticles ($Ag^+$).

TGA weight loss studies were performed on Sample 2 in nitrogen. FIG. 3B displays the TGA data for Sample 2 in nitrogen. The increase in remaining weight is the result of the silver present on the porous support.

Nitrogen Adsorption/Desorption Analysis

Figure 4B:
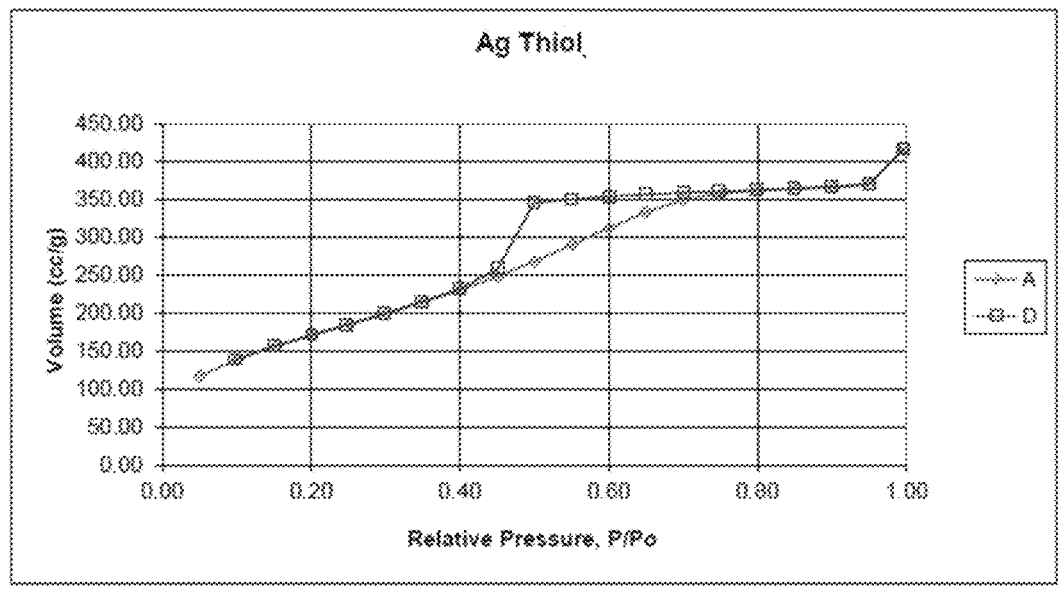
FIG. 4B is a nitrogen adsorption/desorption analysis of an exemplary composition disclosed herein with incorporated transition metal nanoparticles ($Ag^+$). In the figures, "A" represents the adsorption process and "D" represents the desorption process.

Nitrogen adsorption/desorption analysis was performed on Sample 2, and adsorption (line "A") and desorption (line "D") isotherm measurements conducted at 77K are provided in FIG. 4B. The large divergence between relative pressures of about 0.43 to about 0.7 indicates the presence of mesoporosity. While the maximum sorption capacity decreases as a result of the presence of the heavy silver nanoparticles, the overall surface area is not affected. Additionally, the presence of the hysteretic loop in the desorption branch indicates the mesopores have been maintained during the treatment.

Example 3

Oxidation of MOS—SH to Form MOS—SO$_3$H 0.350 grams of MOS—SH prepared in a manner similar to that outlined in Example 1 above were suspended in 10 mL of a 30 wt. % solution of hydrogen peroxide in water. This suspension was stirred overnight at 60° C. The solution was then acidified with 0.25 mL of $H_2SO_4$ and stirred for an additional two hours. The acidified solids were washed with water and methanol and allowed to air dry (hereinafter referred to as Sample 3). Sample 3 was characterized with $^{13}C$ CPMAS NMR, $^{1}H$ MAS NMR, and $^{29}Si$ MAS NMR with the results shown in FIG. 7, before and after treatment with hydrogen peroxide. From left to right, $^{13}C$ CPMAS NMR, $^{1}H$ MAS NMR, and $^{29}Si$ MAS NMR are shown. From bottom to top shows the NMR characterizations of MOS—SH before treatment with hydrogen peroxide (bottom), after treatment with hydrogen peroxide (middle), and before and after superimposed on one another (top).

Figure 7:
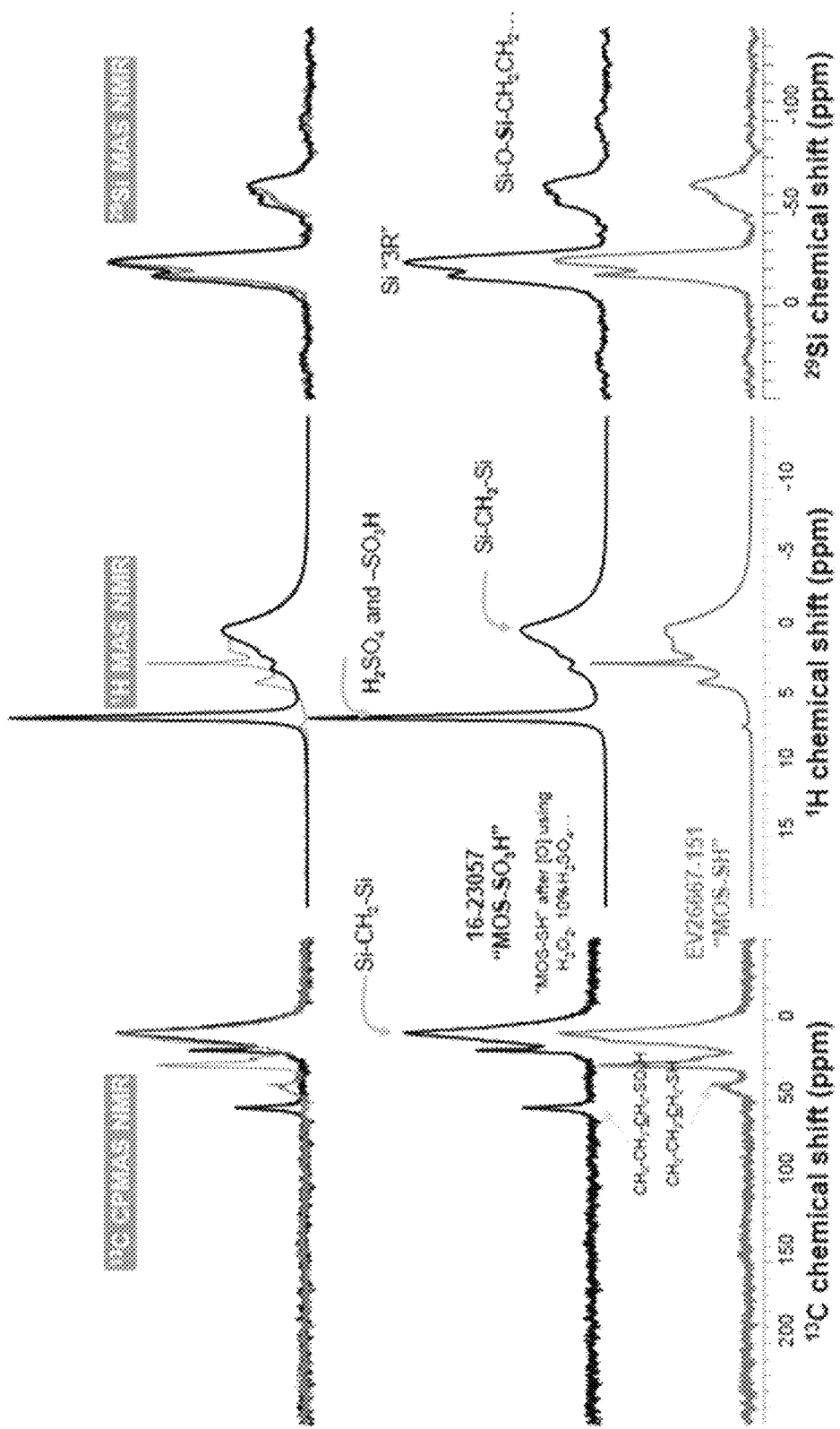
FIG. 7 depicts, through various nuclear magnetic resonance (NMR) spectroscopy techniques, the oxidation of an exemplary composition disclosed herein such that a thiol group is replaced with a sulfonic acid group.

As seen in FIG. 7, oxidation of the carbon directly bound to the sulfur shifts from approximately 28 ppm to 18 ppm. This is the direct result of the oxidation of the sulfur group into a sulfonate. Mirroring these results, the loss of the $CH_2$ resonance in the $^{1}H$ NMR at 2.8 ppm indicates the loss of the thiol functionality after oxidation. While the organic components show the effect of this transformation, there is little to no appreciable shift in $^{29}Si$ MAS NMR indicating that only the thiol of the MOS—SH is affected by the oxidation leaving the framework largely intact.

The invention claimed is:

1. An organosilica material comprising a copolymer of at least one monomer of Formula $[R^1R^2SiCH_2]_3$ (I), wherein:
   $R^1$ represents a $C_1$-$C_4$ alkoxy group; and
   $R^2$ is a $C_1$-$C_4$ alkoxy group or a $C_1$-$C_4$ alkyl group; and
   at least one other monomer of Formula $[(Z^1O)_xZ^2_{3-x}Si—Z^3—SZ^4]$ (II), wherein:
   $Z^1$ represents a hydrolysable functional group;
   $Z^2$ represents a $C_1$-$C_{10}$ alkyl or aryl group;
   $Z^3$ represents a $C_2$-$C_{11}$ cyclic or linear hydrocarbon;
   $Z^4$ is either H or $O_3H$; and
   x represents any one of integers 1, 2, and 3.

2. The organosilica material of claim 1, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom.

3. The organosilica material of claim 1, further comprising a catalyst metal.

4. The organosilica material of claim 3, wherein the catalyst metal comprises a transition metal, a metal oxide, a metal sulphide, or mixtures thereof.

5. The organosilica material of claim 3, wherein the catalyst metal is incorporated as dispersed metal particles.

6. The organosilica material of claim 3, wherein the catalyst metal comprises silver.

7. The organosilica material of claim 1, wherein the at least one monomer of Formula $[R^1R^2SiCH_2]_3$ (I) is 1,1,3,3,5,5-hexaethoxy-1,3,5-trisilacyclohexane ($[(EtO)_2SiCH_2]_3$).

8. The organosilica material of claim 1, wherein the at least one other monomer of Formula $[(Z^1O)_xZ^2_{3-x}Si—Z^3—SZ^4]$ (II) is 3-(triethoxysilyl)propane-1-thiol.

9. A method for separation of olefins from paraffins comprising:
   contacting a hydrocarbon stream comprising olefins and paraffins with an adsorbent bed to produce a paraffins rich stream,
   wherein the adsorbent bed comprises:
     (i) an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3;
     (ii) at least one catalyst metal.

10. The method of claim 9, wherein the at least one catalyst metal is silver.

11. The method of claim 9, wherein the at least one catalyst metal is copper.

12. A hydrogenation process for a hydrocarbon feedstream comprising:
   contacting a hydrocarbon feedstream with a hydrogenation catalyst in the presence of a hydrogen-containing treat gas in a reaction stage operated under effective hydrogenation conditions,
   wherein the hydrogenation catalyst comprises:
     (i) an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3;
     (ii) at least one catalyst metal.

13. The process of claim 12, wherein the organosilica material support further comprises a surface metal on a surface of the organosilica material, the surface metal including aluminum.

14. The process of claim 12, wherein the organosilica material support further comprises an aluminum component, the aluminum component being provided within an aqueous mixture used to form the organosilica material.

15. A method for separation of polar organic compounds from a hydrocarbon feed comprising:
   contacting the hydrocarbon stream comprising polar organic compounds with an adsorbent bed to produce a hydrocarbon stream with a reduced concentration of polar organic compounds,
   wherein the adsorbent bed comprises an organosilica material support, which is a copolymer of at least one monomer of Formula $[R^1R^2SiCH_2]_3$ (I), wherein $R^1$ represents a $C_1$-$C_4$ alkoxy group and $R^2$ is a $C_1$-$C_4$ alkoxy group or a $C_1$-$C_4$ alkyl group, and at least one other monomer of Formula $[(Z^1O)_xZ^2_{3-x}Si—Z^3—SZ^4]$ (II), wherein $Z^1$ represents a hydrolysable functional group; $Z^2$ represents a $C_1$-$C_{10}$ alkyl or aryl group; $Z^3$ represents a $C_2$-$C_{11}$ cyclic or linear hydrocarbon, wherein $Z^3$ has incorporated within the $C_2$-$C_{11}$ cyclic or linear hydrocarbon (a) an amine, (b) an ether, (c) a heteroatom, (d) a combination of any of (a), (b), and (c), or none of (a), (b), and (c), provided that Si and S remain bonded to a carbon atom; $Z^4$ is either H or $O_3H$; and x represents any one of integers 1, 2, and 3.

* * * * *